(12) United States Patent
Gutman et al.

(10) Patent No.: US 7,683,071 B2
(45) Date of Patent: *Mar. 23, 2010

(54) COMPOSITION AND METHOD FOR IMPROVED BIOAVAILABILITY AND ENHANCED BRAIN DELIVERY OF 5,5-DIPHENYL BARBITURIC ACID

(75) Inventors: Daniella Gutman, Rishon Lezion (IL); Barrie Levitt, Mamaroneck, NY (US); Daniel Moros, Larchmont, NY (US); Avraham Yacobi, Englewood, NJ (US); Howard Rutman, New York, NY (US)

(73) Assignee: Taro Pharmaceuticals Industries Ltd., Haifa Bay (IL)

( * ) Notice: Subject to any disclaimer, the term of this patent is extended or adjusted under 35 U.S.C. 154(b) by 697 days.

This patent is subject to a terminal disclaimer.

(21) Appl. No.: 11/201,024

(22) Filed: Aug. 10, 2005

(65) Prior Publication Data
US 2006/0122208 A1    Jun. 8, 2006

Related U.S. Application Data

(63) Continuation-in-part of application No. 10/865,428, filed on Jun. 10, 2004, and a continuation-in-part of application No. 10/735,514, filed on Dec. 11, 2003, now Pat. No. 7,166,610, and a continuation-in-part of application No. 10/354,146, filed on Jan. 30, 2003, now Pat. No. 6,939,873, which is a continuation of application No. 10/333,957, filed as application No. PCT/US01/23420 on Jul. 26, 2001, now Pat. No. 6,756,379.

(60) Provisional application No. 60/600,327, filed on Aug. 10, 2004, provisional application No. 60/432,470, filed on Dec. 11, 2002, provisional application No. 60/352,273, filed on Jan. 30, 2002, provisional application No. 60/221,672, filed on Jul. 26, 2000.

(51) Int. Cl.
*A61K 31/515* (2006.01)
*C07D 239/62* (2006.01)
*C07D 239/64* (2006.01)

(52) U.S. Cl. ...................................... 514/270; 544/305
(58) Field of Classification Search .................. None
See application file for complete search history.

(56) References Cited

U.S. PATENT DOCUMENTS

| 1,960,170 A | 5/1934 | Schnider |
|---|---|---|
| 2,673,205 A | 3/1954 | Hoffmann et al. |
| 3,679,683 A | 7/1972 | Gorbaty |
| 3,711,607 A | 1/1973 | Vida et al. |
| 3,900,475 A | 8/1975 | Vida et al. |
| 3,904,627 A | 9/1975 | Vida et al. |
| 3,919,427 A | 11/1975 | Vida et al. |
| 3,930,006 A | 12/1975 | Wiggins et al. |
| 3,948,896 A | 4/1976 | Vida |
| 4,029,662 A | 6/1977 | Vida |
| 4,046,894 A | 9/1977 | Samour et al. |
| 4,060,528 A | 11/1977 | Janssen et al. |
| 4,260,769 A | 4/1981 | Stella et al. |
| 4,578,503 A | 3/1986 | Ishikawa et al. |
| 4,628,056 A | 12/1986 | Levitt et al. |
| 4,833,148 A | 5/1989 | Olney |
| 4,894,459 A | 1/1990 | Bod et al. |
| 4,914,226 A | 4/1990 | Di Trapani et al. |
| 5,120,850 A | 6/1992 | Bod et al. |
| 5,128,477 A | 7/1992 | Bod et al. |
| 5,456,851 A | 10/1995 | Liu et al. |
| 5,474,990 A | 12/1995 | Olney et al. |
| 5,750,766 A | 5/1998 | Krummel et al. |
| 5,756,815 A | 5/1998 | Knell |
| 5,808,066 A | 9/1998 | Krummel et al. |
| 5,985,856 A | 11/1999 | Stella et al. |
| 6,051,737 A | 4/2000 | Kim et al. |
| 6,093,820 A | 7/2000 | Gutman et al. |
| 6,156,925 A | 12/2000 | Meyer et al. |
| 6,184,238 B1 | 2/2001 | Takano et al. |

(Continued)

FOREIGN PATENT DOCUMENTS

| DE | 946 804 | 8/1956 |
|---|---|---|
| DE | 11 00 639 | 3/1961 |
| DE | 11 03 339 | 3/1961 |
| DE | 1939787 | 2/1970 |
| DE | 2622981 | 12/1977 |
| DE | 4028040 | 3/1992 |
| EP | 726252 | 8/1996 |
| EP | 1 083 172 | 3/2001 |
| GB | 966098 | 8/1959 |
| WO | WO 99/18084 | 4/1999 |
| WO | WO 01/39779 | 6/2001 |
| WO | WO 01/79185 | 10/2001 |
| WO | WO 02/07729 | 1/2002 |
| WO | WO 03/063872 | 8/2003 |
| WO | WO 2004/052350 | 6/2004 |
| WO | WO 2006/003651 | 1/2006 |
| WO | WO 2006/026095 | 3/2006 |

OTHER PUBLICATIONS

Raines et al., Differential Selectivity of Several Barbiturates on Experimental Seizures and Neurotoxicity in the Mouse Epilepsia (1979) vol. 20, pp. 105-113.*

(Continued)

*Primary Examiner*—Shaojia Anna Jiang
*Assistant Examiner*—Eric S Olson
(74) *Attorney, Agent, or Firm*—Venable LLP; Michael A. Gollin; Keith G. Haddaway

(57) ABSTRACT

The present invention relates to a composition and a method of delivering a barbituric acid derivative to the central nervous system of a mammal in need of treatment for neurological conditions. In particular, the present invention relates to a method of administering an oral dosage form of a sodium salt of 5,5-diphenyl barbituric acid to enhance the bioavailability of 5,5-diphenyl barbituric acid and brain delivery of same.

49 Claims, 12 Drawing Sheets

U.S. PATENT DOCUMENTS

| | | | |
|---|---|---|---|
| 6,262,067 B1 | 7/2001 | Allen et al. | |
| 6,281,207 B1 | 8/2001 | Richter et al. | |
| 6,372,757 B1 | 4/2002 | Johns et al. | |
| 6,638,528 B1 | 10/2003 | Kanios | |
| 6,664,262 B2 | 12/2003 | Gutman et al. | |
| 6,756,379 B2 | 6/2004 | Moros et al. | |
| 6,906,079 B2 | 6/2005 | Gutman et al. | |
| 6,939,873 B2 | 9/2005 | Gutman et al. | |
| RE38,934 E | 1/2006 | Gutman et al. | |
| 7,064,205 B2 | 6/2006 | Gutman et al. | |
| 7,166,610 B2* | 1/2007 | Moros | 514/270 |
| 7,227,021 B2 | 6/2007 | Gutman et al. | |
| 2003/0018080 A1 | 1/2003 | Gutman et al. | |
| 2003/0153589 A1 | 8/2003 | Moros et al. | |
| 2003/0187005 A1 | 10/2003 | Gutman et al. | |
| 2004/0167358 A1 | 8/2004 | Gutman et al. | |
| 2004/0186120 A1 | 9/2004 | Moros | |
| 2004/0224947 A1 | 11/2004 | Moros et al. | |
| 2006/0004031 A1 | 1/2006 | Gutman et al. | |
| 2006/0035915 A1 | 2/2006 | Gutman et al. | |
| 2006/0122208 A1 | 6/2006 | Gutman et al. | |
| 2006/0205747 A1 | 9/2006 | Moros et al. | |
| 2006/0258864 A1 | 11/2006 | Gutman et al. | |
| 2007/0072886 A1 | 3/2007 | Moros | |
| 2007/0167624 A1 | 7/2007 | Gutman et al. | |

OTHER PUBLICATIONS

"Remington: The Science and Practce of Pharmacy" 20th edition, published 2000 by Lippincott Williams and Wilkins, pp. 704-712.*
Samour, Carlos M., "Anticonvulsants. 1. Alkoxymethyl derivatives of barbiturates and dipheylhydantoin", Journal of Medicinal Chemistry 14 (3), (1971), p. 187-189.
McElvain, et al "5,5-Diphenylbarbituric Acid" (J. Am. Chem. Soc.) 1935, 57: 1301-04.
Merritt, et al "Experimental determination of anticonvulsive activity of chemical compounds" (Epilepsia) 1945, 3: 51-75.
Alles, et al "Comparative central depressant actions of some 5-phenyl-5-alkyl-barbituric acid" (J. Pharmacol.) 1947, 89: 356-367.
Raines, et al "A comparison of the anticonvulsant, neurotoxic and lethal effects of diphenylbarbituric acid, phenobarbital . . ." (Journal of Pharmacology) 1973, 186: 315-322.
Raines, et al "The effects of 5,5-diphenyl-barbituric acid on experimental seizures in rats: correlation between plasma & brain concentrations . . ." (Epilepsia) 1975,16: 575-581.
Goodman & Gilman's "The Pharmacological Basis of Therapeutics 2001", p. 417 Tenth Ed.
Zavadil III, et al "Diphenylbarbituric Acid" (Epilepsia) 1985, 26: 158-166.
Gibaldi, et al "Pharmacokinetics Second Ed" 2nd Ed Marcel Dekker, Inc. 1982.
Yeh, et al "A comparison of numerical integrating algorithms by trapezoidal, lagrange, and spline approximations." (J. Pharmacokinet Biopharm) 1978, 6: 79.
Glazko, et al "Early adventures in drug metabolism: 2. The absorption of drugs" (Ther. Drug Monit) 1987, 9: 80-89.
Corkill, et al "Timing of pentobarbital administration for brain protection in experimental stroke" (Neurol. Surg.) 1976, 5: 147-149.
Hoff, et al "Barbiturate protection from cerebral infarction in primates" (Stroke) 1975, 6: 28-33.
Levy, et al "Delayed pentobarbital administration limits ischemic brain damage in gerbils" (Annals of Neurology) 1979, 5(1): 59-64.
Lightfoote, et al "Modification of cerebral ishcemic damage by anesthetics" (Stroke) 1977, 8: 627-628.
Raines, et al "Serum and brain levels of 5,5-diphenylbarbituric acid (DPB) after administration of dimethoxymethyl . . ." (Epilepsia) 1996, 37:suppl. 5, Abstract 1.84.
Raines, et al "Conversion of dimethoxymethyl-diphenylbarbituric acid (DMMDPB) to diphenylbarbituric acid (DPB) in the rat" (The FASEB J.) 1996, Abstract No. 895.

Breimer, et al "Pharmacokinetics and relative bioavailability of heptabarbital and heptabarbital sodium after oral admin . . ." ( Eur. J. Clin. Pharmacology) 1975, 9: 169-178.
Alles, et al "Comparative central depressant actions of some 5-phenyl-5-alky barbituric acids" (J. Pharmacol Exp. Ther.) 1947, 89: 356-367.
Raines, et al "Pre and postjunctional effects of diphenylhydantoin at the cat soleus neuromuscular junction" (J. Pharmacol Exp. Ther.) 1966, 153: 361-366.
Baumel, et al "Metabolism and anticonvulsant properties of primidone in the rat" (J. Pharmacol Exp. Ther.) 1973, 186: 305-314.
Craig, et al "Metabolism and anticonvulsant properties of mephobarbital and phenobarbital in rats" (J. Pharmacol Exp. Ther.) 1971, 176: 35-41.
Fink, et al "Modification of maximal audiogenic and electroshock seizures in mice by psychopharmacologic drugs" (J. Pharmacol Exp. Ther.) 1959, 127: 318-324.
Knoefel, et al "The anticonvulsant action of diphenylhydatoin and some related compounds" (J. Pharmacol Exp. Ther) 1942, 76: 194-201.
Prankerd, et al "Physio-chemical properties of barbituric acid derivatives: IV. Solubilities of 5,5-disubstituted barbituric acids . . ." (Int. J. Pharmaceutics) 1994, 112: 1-15.
Nims, et al Comparative pharmacodynamics of hepatic cytochrome P450 2B induction by 5,5-diphenyl- and 5,5-diethyl-substituted . . . (J. Pharmacol Exp. Ther.) 1994, 270: 348-355.
Iadarola, et al "Comparison of the effects of diphenylbarbituric acid, phenobarbital, pentobarbital and secobarbital . . ." (J. Pharmacol Exp. Ther.) 1985, 232: 127-133.
Glazko, AJ "Diphenylhydatoin" (Pharmacology) 1972, 8: 163-177.
Serrano, et al "Intramuscular administration of diphenylhydantoin" 1974, 31: 276-277.
Whittle, et al "Differential effect of sedative and anticonvulsant barbiturates on specific gaba binding to membrane prep . . ." (Bio. Pharmacology) 1982, 31: 2891-895.
Dox, et al "5,5-Diarylbarbituric Acids" (J. Chem. Soc.) 1923, 45: 1811-1816.
McKeown, et al "Thermodynamic functions for dissociation of 5,5-disubstituted barbituric acids-their significance in structure-reactivity . . ." (Ellis Horwood) 1986, 6: 80-89.
Raines, et al "Anticonvulsant properties of 5,5-diphenylbarbituric acid (DPB)" (Pharmacology) 1973, 32: 3246.
EP Search Report, Jun. 16, 2005.
Pharmaceutical Chemistry, Mar. 7, 1981.
Office Action issued by the USPTO on Nov. 1, 2007 for U.S. Appl. No. 10/865,428.
Office Action issued by the USPTO on Oct. 5, 2007 for U.S. Appl. No. 11/355,336.
Office Action issued by the USPTO on Sep. 28, 2007 for U.S. Appl. No. 11/355,339.
Office Action issued by the USPTO on Jan. 11, 2008 for U.S. Appl. No. 11/727,557.
International Search Report issued in PCT Application No. PCT/US04/041138, mailed on Aug. 10, 2005.
Written Opinion issued in PCT Application No. PCT/US04/041138, mailed on Aug. 10, 2005.
European Search report issued in EP Application No. 03 01 1817, completed Jul. 14, 2003.
European Search report issued in EP Application No. 03 73 5068, dated Feb. 28, 2006.
European Search report issued in EP Application No. 05 78 6192 , dated Nov. 22, 2007.
International Search Report Issued in PCT Application No. PCT/US98/20665, mailed on Apr. 2, 1999.
International Search Report Issued in PCT Application No. PCT/US01/23420, mailed on Nov. 20, 2001.
International Search Report Issued in PCT Application No. PCT/US03/02638, mailed on Jun. 18, 2003.
International Search Report Issued in PCT Application No. PCT/IL2005/000697, mailed on Oct. 13, 2006.
International Search Report Issued in PCT Application No. PCT/US2005/028380, mailed on Dec. 8, 2006.

International Preliminary Examination Report issued in PCT Application No. PCT/US01/23420, completed on Feb. 23, 2003.
International Preliminary Examination Report issued in PCT Application No. PCT/US03/02638, completed on Oct. 31, 2003.
International Preliminary Examination Report issued in PCT Application No. PCT/US03/039530, completed on Mar. 10, 2005.
International Preliminary Report on Patentability issued in PCT Application No. PCT/IL2005/000697, issued on Jan. 9, 2007.
International Preliminary Report on Patentability issued in PCT Application No. PCT/US2005/028380, issued on Feb. 13, 2007.
Goodman & Gilman's The Pharmacological Basis of Therapeutics, 9th Ed., 373-380 (1996).
Kojima, Chem. Pharm. Bull. 21 (11): 2432-2437 (1973).
Kojima et al., J. Pharm Sci. 60: 1639-1641 (1971).
Malhotra, S. et al., "T-2000, a novel non-sedating barbiturate reduces infact size and improves neurologic functions following MCAO in the rat," Program No. 821.10. 2004 Abstract Viewer/Itinerary Planner. Washington, DC: Society for Neuroscience, 2004. Online.
Rekling Jens C., "Neuroprotective effects of anticonvulsants in rat hippocampal slice cultures exposed to oxygen/glucose deprivation", Neuroscience Letters, vol. 335, No. 3, Jan. 2, 2003, pp. 167-170.
Vida J. A. et al, "Anticonvulsants. IV. Metharbital and phenobarbital derivatives" Journal of Medicinal 1378-1381.
Vida J. A. et al, "Anticonvulsants. III. Phenobarbital and mephobarbital derivatives", Journal of Medicinal Chemistry 1973, vol. 16, p. 602-605.
Werner W. et al., "Structure effect interactions in Mannich bases with and without nitrogen mustard groups and some reference compounds as potential immunosuppressive agents", retrieved from STN Database accession No. 85: 72035, Pharmazie 31(5) 282-7, 1976.
Selleri, R. et al., "N1, N3-Disubstituted barbituric acid derviates of gangioplegic or curarelike action", retrieved from STN Database accession No. 1959:111820, Farmaco, Edizione Scientifica, 12, 3-14, 1957.
Casagrande, C. et al., "Synthesis and antiarrhythmic activity of 5,5-disubstituted-3-aminoalkylhydantoins and some heterocyclic and noncyclic analogs", retrieved from STN Database accession No. 1975:43261, Farmaco, Edizione Scientific, 29(10) 757-785, 1974.
Vida J. et al., "Anticonvulsants. 2. Acyloxymethyl and halomehtyl derivaitves of barbituric acid and diphenylhydantoin", Journal of Medicinal Chemistry, 14(3): p. 190-193, Mar. 1971.
Acta Neurol Scand., 1987:75:332-340, "Primidone and Propranolol in Essential Tremor: A Study Based on Quantitative Tremor Recording and Plasma Anticonvulsant Levels", P. Dietrichson, et al.
Aldrich Chemical Catalog, 1990-1991, p. 303.
Appendix 1 of U.S. Appl. No. 60/352,273, filed Jan. 30, 2002: Chemical Derivative Chart (total of 8 pages).
Appendix 2 of U.S. Appl. No. 60/352,273, filed Jan. 30, 2002: References to Chemical Derivatives (total of 3 pages).
Appendix 3 of U.S. Appl. No. 60/352,273, filed Jan. 30, 2002: Cancerlit . . . (total of 9 pages).
Appendix 3 of U.S. Appl. No. 60/352,273, filed Jan. 30, 2002: MEDLINEplus printout of Jan. 15, 2002: Barbiturates (Systemic) (total of 14 pages).
Appendix 3 of U.S. Appl. No. 60/352,273, filed Jan. 30, 2002: PubMed search results printout of Jan. 15, 2002 (total of 7 pages).
Arch Otolaryngol, vol. 110, Jun. 1984, pp. 394-397, "Spastic Dysphonia and Essential (Voice) Tremor Treated With Primidone", David E. Hartman, et al.
Archives of Neurology, Apr. 1999, vol. 56, No. 4: 475-480, Alexandre Gironell, et al., "A Randomized Placebo-Controlled Comparative Trial of Gabapentin and Propranolol in Essential Tremor".
Bashir, K. et al.: "Clozapine for the control of hemiballismus," Clinical Neuropharmacology, vol. 17, No. 5, 1994, pp. 477-480, XP009032005.
Barnes, Harry M. and McElvain, S. M. "For Further Observations on the Condensation of Benzene with Alloxan" (J. Am. Chem. Soc.) Jul.-Dec. 1937, 59: 2348-2351.
Berge et al., "Pharmaceutical Salts" Journal of Pharmaceutical Sciences (1977) vol. 66, No. 1, pp. 1-19.
Bertram et al., "Phenobarbital is superior to phenytoin as an antiepileptic, neuroprotectant and antiepileptogenic agent in a rat model of status epilepticus and chronic limbic epilepsy," Epilepsia, vol. 37, No. Suppl. 5, p. 140 (1996); and Annual Meeting of the American Epilepsy Society, San Francisco, CA, USA, Dec. 7-10, 1996.
Bhardwaj et al., "Pentobarbital inhibits extracellular release of dopamine in the ischemic striatum", Journal of Neural Transmission [Gen Sect], 82, pp. 111-117, (1990).
Boron Tribromide, Encyclopedia of Reagents for Organic Synthesis edited by Leo Pacquette, pp. 1-9, 2003.
Brint et al., "Focal brain ischemia in the rat: Methods for reproducible neocortical infarction using tandem occlusion of the distal middle cerebral and ipsilateral common carotid arteries", J. Cerebral Blood Flow Metab., 8, pp. 474-485, (1988).
C.D. Marsden, Origins of Normal and Pathological Tremor in Movement Disorders: Tremor. Eds. L.J. Findley and R. Capildeo, New York, Oxford University Press, 1984, pp. 37-84 "Origins of Normal and Pathological Tremor".
Casara et al., "Synthesis of acid stable fluorinated acyclonucleosides as potential antiviral agents," Tetrahedron Letters, 32(31) (1991), pp. 3823-3826.
Clinical Neuropharmacology vol. 10, No. 4, 1987, pp. 342-350, Essential Tremor Variants: Effect of Treatment, William C. Koller, et al.
Clinical Neuropharmacology, vol. 13, No. 1, 1990, pp. 67-76, "Primidone in the Long-Term Treatment of Essential Tremor: A Prospective Study with Computerized Quantitative Analysis", Enrico Sasso, et al.
Clinical Neuropharmacology, vol. 13, No. 3, 1990, pp. 210-223, "Basic Mechanism of Action of Drugs Used in the Treatment of Essential Tremor", Xiao-Ming Guan, et al.
Clinician, May 2001, vol. 19, No. 2, pp. 1-15, "Essential Tremor: A Practical Guide to Evaluation, Diagnosis, and Treatment".
Foye, "Principles of Medicinal Chemistry," 3rd ed. (1990) pp. 164, 179.
Gao et al., "Physical Chemical Stability of Warfarin Sodium,"AAPS Pharmasci (2001) 3(1) Article 3.
Garcia et al., "Neurological deficit and extent of neuronal necrosis attributable to middle cerebral artery occlusion in rats. Statistical validation", Stroke, 26(4), pp. 627-634, 1995.
Garcia et al., "Neuronal necrosis after middle cerebral artery occlusion in Wistar rats progresses at different time intervals in the caudoputamen and the cortex", Stroke, 26(4), 636-643 (1995).
Gesson et al., "A practical method for N-alkylation of succinimide and glutarimide", Bull Soc. Chim. Fr. 129, pp. 227-231, (1992).
Ginsberg, "Animal Models of Global and Focal Cerebral Ischemia," Chapter 34 in Welsh KMA et al., Primer on Cerebrovascular Diseases, Academic Press, New York (1997).
Goodman & Gilman's The Pharmacological Basis of Therapeutics, 9th Ed. Ch. 17, 361-396, William R. Hobbs et al., "Hypnotics and Sedatives; Ethanol".
Hamann, M. et al.: "Effects of striatal injections of GABAA receptor agonists and antagonists in a genetic animal model of paroxysmal dystonia," European Journal of Pharmacology, vol. 443, No. 1-3, May 17, 2002, pp. 59-70, XP002284223.
International Search Report issued in PCT Application No. PCt/US03/39530, mailed on Jul. 7, 2004.
Jax® Mice Literature, "Ask the Vet" No. 499 Published online in fall 2005 at http://jaxmice.jax.org/library/notes/499c.html.
Journal of Neurology, Neurosurgery, and Psychiatry 1985;48:911-915, "Primidone in Essential Tremor of the Hands and Head: A Double Blind Controlled Clinical Study", Leslie J. Findley, et al.
Journal of Neurology, Neurosurgery, and Psychiatry 1986;49:64-68, "A Comparison of Primidone, Propranolol, and Placebo in Essential Tremor, Using Quantitative Analysis", W.P. Gorman, et al.
Kamata et al., "Studies of Antitumor-Active 5-Fluorouracil Derivatives I Synthesis of N-Phthalidyl 5-Fluorouracil Derivatives", Chem. Pharm. Bull, 33 (8), pp. 3160-3175, (1985).
Karger et al., "Methoxymethyl Methanesulfonate, A Novel Active Oxyalkylating Agent," J. Am. Chem. Soc., 91:5663 (1969).
Loudon, "Organic Chemistry", Addison-Wesley (1984), pp. 617, 721-722, 1061-1064, 1086-1088, 1194.
Masuda et al., "Relationships Between Plasma Concentrations of Diphenylhydantoin, Phenobarbital, Carbamazepine, and 3-Sulfamoylmethyl-1,2-Benzisoxazole (AD-810), a New Anticonvulsant Agent, and Their Anticonvulsant or Neurotoxic Effects in Experimental Animals", Epilepsia, 20, pp. 623-633, (1979).

Mayo Clinic Proceedings, vol. 66, No. 10, Oct. 1991, pp. 991-997, Manfred D. Muenter, et al. "Treatment of Essential Tremor With Methazolamide".

Merck Manual of Diagnosis and Therapy, Seventeenth Edition, Beers et al., ed., (1999), Chapter 179, pp. 1462-1473.

Miller, ed., "Stroke Therapy: Basic, preclinical, and clinical directions", Wiley (1999).

Modern Pharmacology, 2nd Ed., 1986, Ch. 4, pp. 41-64, Theodore E. Gram "Metabolism of Drugs".

Movement Disorders 2, 1987, (22) 438-458, Leslie J. Findley, "The Pharmacology of Essential Tremor".

Movement Disorders, vol. 13, Suppl 3., pp. 90-100, 1998, Paul G. Wasielewski, et al. "Pharmacologic Treatment of Tremor".

Movement Disorders, vol. 16, No. 3, 2001 pp. 464-468, William C. Koller, et al. "Long Term Safety and Efficacy of Unilateral Deep Brain Stimulation of the Thalamus in Essential Tremor".

Movement Disorders, vol. 6, No. 1, 1991, pp. 65-68, "Quantitative Comparison of Barbiturates in Essential Hand and Head Tremor", Enrico Sasso, et al.

Neurology, 1985, 35:1784-1787, "Phenobarbitone in Essential Tremor", Leslie J. Findley, et al.

Neurology, 1986; 36:121-124, "Efficacy of Primidone in Essential Tremor", William C. Koller, et al.

Neurology, 1988, 38:808-810, "Double-Blind Comparison of Primidone and Phenobarbital in Essential Tremor"; Enrico Sasso, et al.

Neurology, Jun. 2000 vol. 54, Supp.1 4, S30-S38, William C. Koller et al., "Pharmacologic Treatment of Essential Tremor".

Neurology, Jun. 2000, vol. 54, Suppl 4, S8-S13, Leslie J. Findley, "Epidemiology and Genetics of Essential Tremor".

Ondo, W. et al.: "Essential tremor. Treatment Options," CNS Drugs 1996 New Zealand, vol. 6, No. 3, 1996, pp. 178-191, XP009032012.

Parkinson's Disease and Movement Disorders, Urban & Schwarzenberg, Inc., 1988, 17: 225-234, Stanley Fahn, et al. "Clinical Rating Scale for Tremor".

Piatt, et al., "High dose barbiturate therapy in neurosurgery and intensive care," Neurosurgery, vol. 15, No. 3, Sep. 1984, pp. 427-444.

PubMed search results printout of Dec. 27, 2002 (total of 3 pages).

Pulsinelli and Brierley, "A new model of bilateral hemispheric ischemia in the unanesthetized rat", Stroke, May-Jun. 10(3), pp. 267-272, (1979).

Pulsinelli et al., "Temporal profile of neuronal damage in a model of transient forebrain ischemia", Annals of Neurology, May 11(5), 491-498, (1982).

Raines et al., "Conversion of Dimethoxymethyl-Diphenylbarbituric Acid (DMMDPB) to Diphenylbarbituric Acid (DPB) in the Dog," The FASEB J., 13(4):A475, Abstract 394.2 (1999).

Raines et al., Chemical Abstracts, 79:87539k, 1973.

Raines et al., Chemical Abstracts, 92:174402x, 1980.

Remington: The Science and Practice of Pharmacy, 20th Edition; Published 2000 by Lippincott Williams and Wilkins, Edited by Daniel Limmer, pp. 317-322.

Remington: The Science and Practice of Pharmacy, 20th Edition; Published 2000 by Lippincott Williams and Wilkins, Edited by Daniel Limmer, pp. 704-714.

Remington: The Science and Practice of Pharmacy, 20th Edition; Published 2000 by Lippincott Williams and Wilkins, Edited by Daniel Limmer, pp. 743-747.

Remington: The Science and Practice of Pharmacy, 20th Edition; Published 2000 by Lippincott Williams and Wilkins, Edited by Daniel Limmer, pp. 858-863.

Rev. Neurol., 2001, 32 (6): 520-524; I. Balas et al. "*Talamotomia esterotaxica* de la enfermedad de Parkinson y otros tipos de temblor. Experiencias de la actividad multiunitaria burst en el talamo basada en semimicroelectrodos". (English Abstract).

Salmon-Legagneur et al., "Recherches dans la serie des diacides .alpha..alpha.-disubstitues et de leurs derives. III. Les acides .alpha.-phenol .alpha.-alcoyl (ou phenoalcoyl) glutariques et leurs principaux derives", Bull. Soc. Chim. France (1953) p. 70.

Salmon-Legagneur et al., "Sur les acides .alpha.-pheyl .alpha.-alcoyl (ou phenoalcoyl) glutariques", Comptes Rendus de l'Academie des Sciences, (Mar. 3, 1952) p. 1060.

Shapiro, "Barbiturates in Brain Ischaemia," British Journal of Anaesthesia, BJM Publishing Group, London, Great Britain, vol. 57, No. 1, Jan. 1985, pp. 82-95.

Sircar, "CLXXIII.—The Influence of Groups and Associated Rings on the Stability of Certain Heterocyclic Systems. Part II. The Substituted Succinimides"; Journal of the Chemical Society, MA 1927, pp. 1252-1258.

Stavber et al., Chemical Abstracts, 99:157381s, 1983.

Sturfelt, G. et al.: Acute Effects of Barbiturates in Parkinson's Disease, "Acta Medica Scandinavica, Almqvist & Wiksell Periodical Co.;" Stockholm, SE, vo. 201, No. 1/2, 1977, pp. 75-76, XP000937405.

Swanson et al., "Barbiturates impair astrocyte glutamate uptake," GLIA, Dec. 1998, vol. 34, No. 4, Dec. 1998, pp. 365-371.

Tagmann et al., Helv. Chim. Acta 35, 1541-1549 (1952).

Thacker et al., "Method for the Determination of 5,5-Diphenylbarbituric Acid and Separation from 1,3-Dimethoxymethyl-5,5-Diphenylbarbituric Acid in Plasma by High Performance Liquid Chromatography," J. Chromatography B. 710:149-155 (1998).

The Merck Index, 10th Ed., (Merck & Co., Inc., Rahway, NJ) (1983) p. 544 (entry 3694).

The New England Journal of Medicine, vol. 339, No. 16, Oct. 1998, pp. 1130-1143, Anthony E. Lang, et al. "Parkinson's Disease", Second of Two Parts.

The New England Journal of Medicine, vol. 345, No. 12, Sep. 2001 pp. 887-891, Elan D. Louis, "Essential Tremor".

Weinryb et al., Chemical Abstracts, 76:1206c, 1972.

European Search report issued in EP Application EP 01 95 9195, dated Feb. 24, 2006.

Zavadil et al., Effects of Diphenylbarbituric Acid on Neuromuscular and Spinal Cord Function in the Cat, Neuroscience Abstracts, p. 694 (1975).

Broderick et al., "Guidelines for the Management of Spontaneous Intracerebral Hemorrhage," Stroke, vol. 30, pp. 905-915, 1999.

IUPAC, Glossary of terms used in Medicinal Chemistry, pp. 1-10, 1998.

Office Action issued by the USPTO on Apr. 22, 2009 for U.S. Appl. No. 10/865,428.

Constantino et al., "Metabotropic glutamate receptors: targets for therapy of cerebral ischaemia," Expert Opinion on Therapeutic Drugs, vol. 5, pp. 669-683, 2001.

Office Action Issued by the USPTO on Mar. 24, 2009, for U.S. Appl. No. 11/169,044.

Office Action Issued by the USPTO on Mar. 6, 2009, for U.S. Appl. No. 11/355,339.

Office Action Issued by the USPTO on Feb. 25, 2009, for U.S. Appl. No. 11/355,336.

Doak et al., Pharmacotherapy, vol. 18, No. 3, pp. 637-645, 1998.

Glazco et al., Therapeutic Drug Monitoring, vol. 5, No. 4, pp. 409-417, 1983. (Abstract only).

Depakene Product Information, Abbott Laboratories, revised Apr. 2009.

Office Action Issued by the USPTO on Jul. 8, 2009, for U.S. Appl. No. 10/865,428.

Office Action Issued by the USPTO on Sep. 8, 2009, for U.S. Appl. No. 11/355,336.

Meriam Webster's Collegiate Dictionary, Tenth Edition, published 1998 by Merriam-Webster, Incorporated, pp. 924 and 935.

The Merck Manual of Diagnosis and Therapy, Seventeenth Edition, Published 1999 by Merck Research Laboratories, pp. 1421-1425.

Office Action Issued by the USPTO on Dec. 28, 2009, for U.S. App. No. 10/865,428.

Ukkola et al., "Epilepsy After Operative Treatment of Ruptured Cerebral Aneurysms," Acta Neurochirurgica, vol. 106, pp. 115-118, 1990.

* cited by examiner

COMPOSITION AND METHOD FOR IMPROVED BIOAVAILABILITY AND ENHANCED BRAIN DELIVERY OF 5,5-DIPHENYL BARBITURIC ACID

CROSS REFERENCE TO RELATED APPLICATIONS

This application claims the benefit under 35 U.S.C. §1.119(e) of Provisional Application Ser. No. 60/600,327 filed Aug. 10, 2004, and is a Continuation-In-Part (CIP) of U.S. Ser. No. 10/735,514, filed Dec. 11, 2003 now U.S. Pat. No. 7,166,610, which claims the benefit of Provisional Application Ser. No. 60/432,470, filed Dec. 11, 2002, and is a CIP of U.S. Ser. No. 10/354,146, filed Jan. 30, 2003 now U.S. Pat. No. 6,939,873, which claims the benefit of Provisional Application Ser. No. 60/352,273, filed Jan. 30, 2002, and is a CIP of U.S. Ser. No. 10/865,428, filed Jun. 10, 2004, which is a continuation of U.S. Ser. No. 10/333,957, filed Jan. 27, 2003 and issued as U.S. Pat. No. 6,756,379, which is a national phase of PCT/US01/23420, filed Jul. 26, 2001, which claims the benefit of Provisional Application Ser. No. 60/221,672, filed Jul. 26, 2000, the disclosures of all of which are incorporated by reference herein in their entirety.

FIELD OF THE INVENTION

The present invention relates to a composition and a method for providing improved bioavailability and enhanced delivery of a barbituric acid derivative to the central nervous system of a mammal. In particular, the present invention relates to methods of administering an oral dosage form comprising a salt of 5,5-diphenyl barbituric acid selected from the group consisting of sodium, potassium and lithium to produce efficacious levels of 5,5-diphenyl barbituric acid in the blood and brain of a mammal.

BACKGROUND OF THE INVENTION 5,5-diphenyl barbituric acid (DPB) is a member of the non-sedating barbiturates and a metabolite of 1,3-dimethoxymethyl-5,5-diphenyl-barbituric acid (DMMDPB) and monomethoxymethyl-5,5-diphenylbarbituric acid (MMMDPB). Since DPB synthesis was first reported in 1935, the therapeutic use of 5,5-diphenyl barbituric acid (DPB) was overlooked, in part because of its lack in purported hypnotic activities. (McElvain et al. "5,5-Diphenylbarbituric Acid" *J. Am. Chem. Soc.* 1935, 57:1301-04). DPB was found to be effective only in exceedingly large doses and therefore no pharmacological application was suggested. DPB has the following structure, and it exists as a free acid form.

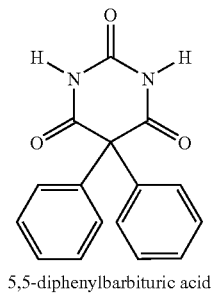

5,5-diphenylbarbituric acid

In 1973, Raines et al. re-evaluated the anticonvulsant effects of DPB in a mouse model using the maximal electroshock seizure (MES) test. ("A comparison of the anticonvulsant, neurotoxic and lethal effects of diphenylbarbituric acid, phenobarbital and dipheylhydantoin in the mouse" *Journal of Pharmacology* 1973, 186: 315-322). DPB, given by stomach tube, was effective in protecting mice from seizure induced either by electroshock or pentylenetetrazole (a chemical convulsant). However, it was not possible to give enough DPB via stomach tube to produce neurotoxicity or death, as the poorly soluble DPB (free acid form) could not be adequately absorbed to achieve these latter end-points. In subsequent rat studies, Raines et al. monitored plasma and brain concentrations of DPB and speculated that DPB (free acid form) is probably slowly absorbed from the gastrointestinal tract and slowly moves into the brain to provide an anti-seizure activity. ("The effects of 5,5-diphenyl-barbituric acid on experimental seizures in rats: correlation between plasma and brain concentrations and anticonvulsant activity" *Epilepsia,* 1975, 16:575-581).

DPB is not a viable oral therapeutic agent, in large part because of the problems associated with its poor bioavailability. Water solubility of DPB is known to be exceedingly poor, 1/100 fold less soluble as compared to phenobarbital in aqueous solution at pH 7. (See, *Epilepsia,* 1973, 186, 315-22). DPB free acid has been administered orally as an insoluble form (i.e., suspension).

Despite substantial effort, there has been no success in improving the bioavailability of DPB. This includes exploring alternative routes of administration. To this end, Raines et al. compared the intraperitoneal and oral administrations of DPB (free acid form) and correlated the plasma DPB concentrations with the anticonvulsant activity. ("The effects of 5,5-diphenyl barbituric acid on experimental seizures in rats: correlation between plasma and brain concentrations and anticonvulsant activity" *Epilepsia,* 1975, 16, 575-81). It was found that oral gavage of DPB (free acid form) is considerably less potent when compared to intraperitoneal administration of DPB, which correlates well with the observation that oral absorption for DPB is poor. Despite a better bioavailability, intraperitoneal administration does not represent a practical therapeutic route.

To circumvent the low absorption problems associated with DPB, Raines et al. examined the preparation of a DPB saline solution for intravenous administration. (*Epilepsia,* 1985, 26: 158-166). Sodium hydroxide is required to keep DPB in solution, resulting in a high pH of about 10.5 to about 12 for the solution. Intravenous administration or oral administration of such an alkaline solution would cause significant tissue necrosis, and thus does not represent a feasible choice for safe patient use. Other than the known intravenous and intraperitoneal administrations of DPB (free acid forms), there is no other known dosage form of DPB that would provide good bioavailability in a mammal and hence permit optimal and sustained circulating levels of DPB.

To this end, several efforts have been made to use DMMDPB and MMMDPB as prodrugs in attempt to provide blood levels of DPB to treat neurological diseases. For example, U.S. Pat. No. 6,756,379 discloses the use of DMMDPB and MMMDPB against neurological conditions including, inter alia, cerebral ischemia, head trauma, stroke, and epilepsy. WO 2004/052350 describes the use of DMMDPB, and MMMDPB against movement disorders; more specifically, essential tremor. The use of DMMDPB and MMMDPB as a prodrug for DPB has required larger doses of prodrug (because of poor bioavailability) to provide an optimal, steady blood level of DPB. Poor bioavailability may lead to intra- and inter-individual variability. Variable serum levels are not desirable because it may increase the incidence of break-through seizures and adverse effects produced by excessive drug levels.

There is a continuing need to provide a composition and a method for improved bioavailability of DPB and enhancing brain delivery of the same to the central nervous system in mammals. We report herein a reliable synthesis of salt forms of DPB and production of an oral solid dosage form of a DPB salt. Surprisingly, an oral dosage of DPB salts, in contrast to its free acid counterpart, provides a high and sustained blood level of DPB and enhances brain delivery of DPB so that it can exert its effects in the central nervous system. An improved bioavailability of DPB is believed to contribute to its beneficial effects in the treatment of neurological conditions.

SUMMARY OF THE INVENTION

It is an object of the present invention to provide an enhanced and efficient delivery of a barbituric acid derivative (i.e., DPB) to the central nervous system in a mammal by administrating an isolated salt form of DPB in an oral dosage form. Preferably, the oral dosage form is a solid, dry dosage form. Preferably, the salt form of DPB is a salt selected from the group consisting of sodium, potassium and lithium. Preferably, the sodium salt of DPB is administered at a dose sufficient to ensure a sustained therapeutic plasma concentration of DPB in a human with a neurological condition.

It is another object of the present invention to provide a method whereby a salt form of barbituric acid derivative (i.e., DPB) is utilized to deliver DPB to the central nervous system (i.e., through the blood-brain barrier) and thus entering the central nervous system and cerebrospinal fluid.

It is another object of the present invention to provide a method for treating a neurological condition comprising the step of administering an isolated salt form of DPB so as to deliver DPB to the central nervous system. Preferably, the isolated salt form is sodium DPB.

It is yet another object of the present invention to provide a composition comprising an isolated salt form of DPB that can be used to improve in vivo delivery of DPB. In particular, the present oral dosage form provides the advantages of improved bioavailability and increased brain delivery of DPB in vivo.

Accordingly, the present invention provides a method for treating a neurological condition in a mammal, comprising the step of administering an oral dosage form that comprises a salt form of 5,5-diphenyl barbituric acid to a mammal in a sufficient amount to provide an efficacious blood level of 5,5-diphenyl barbituric acid. Preferably, the oral dosage form contains an isolated sodium salt of DPB.

In accordance with the present invention, the improved bioavailability may be characterized by an $AUC_{0-48}$ of 5,5-diphenyl barbituric acid of at least 800 μg·hr/mL. Preferably, the improved bioavailability is characterized by an $AUC_{0-48}$ of 5,5-diphenyl barbituric acid of at least 1,200 μg·hr/mL. Preferably, the improved bioavailability is characterized by an $AUC_{0-48}$ of 5,5-diphenyl barbituric acid of at least 1,500 μg·hr/mL.

In accordance with the present invention, the improved bioavailability may further be characterized by a $C_{max}$ of 5,5-diphenyl barbituric acid of at least 50 μg/mL. Preferably, the improved bioavailability may further be characterized by a $C_{max}$ of 5,5-diphenyl barbituric acid of at least 75 μg/mL. Preferably, the improved bioavailability may further be characterized by a $C_{max}$ of 5,5-diphenyl barbituric acid of at least 100 μg/mL.

In accordance with the present invention, a salt form of 5,5-diphenyl barbituric acid is shown to have an improved bioavailability when compared to that of a free acid form. Preferably, the improved bioavailability is characterized by an $AUC_{0-48}$ of 5,5-diphenyl barbituric acid that is at least about 1.5 times greater than that provided by oral administration of the same amount of a free acid form of 5,5-diphenyl barbituric acid.

More preferably, the $AUC_{0-48}$ of 5,5-diphenyl barbituric acid is at least about 2 times greater than that provided by oral administration of the same amount of a free acid form of 5,5-diphenyl barbituric acid. More preferably, the $AUC_{0-48}$ of 5,5-diphenyl barbituric acid is at least about 3 times greater than that provided by oral administration of the same amount of a free acid form of 5,5-diphenyl barbituric acid. More preferably, the $AUC_{0-48}$ of 5,5-diphenyl barbituric acid is at least about 3.5 times greater than that provided by oral administration of the same amount of a free acid form of 5,5-diphenyl barbituric acid.

Preferably, the improved bioavailability is further characterized by a $C_{max}$ of 5,5-diphenyl barbituric acid that is at least about 1.25 times greater than that provided by oral administration of the same amount of a free acid form of 5,5-diphenyl barbituric acid.

Preferably, the $C_{max}$ of 5,5-diphenyl barbituric acid is at least about 1.5 times greater than that provided by oral administration of the same amount of a free acid form of 5,5-diphenyl barbituric acid. More preferably, the $C_{max}$ of 5,5-diphenyl barbituric acid is at least about 2 times greater than that provided by oral administration of the same amount of a free acid form of 5,5-diphenyl barbituric acid. More preferably, the $C_{max}$ of 5,5-diphenyl barbituric acid is at least about 2.5 times greater than that provided by oral administration of the same amount of a free acid form of 5,5-diphenyl barbituric acid.

Preferably, the salt form of 5,5-diphenyl barbituric acid is sodium 5,5-diphenyl barbiturate, potassium 5,5-diphenyl barbiturate or lithium 5,5-diphenyl barbiturate. More preferably, the salt form of 5,5-diphenyl barbituric acid is sodium 5,5-diphenyl barbiturate.

Preferably, the salt form of 5,5-diphenyl barbituric acid is administered in a sufficient amount to provide a brain concentration of 5,5-diphenyl barbituric acid that is at least about 1.5 times greater than that provided by oral administration of the same amount of a free acid form of 5,5-diphenyl barbituric acid. More preferably, the brain concentration of 5,5-diphenyl barbituric acid is at least about 2 times greater than that provided by oral administration of the same amount of a free acid form of 5,5-diphenyl barbituric acid. More preferably, the brain concentration of 5,5-diphenyl barbituric acid is at least about 3 times greater than that provided by oral administration of the same amount of a free acid form of 5,5-diphenyl barbituric acid. More preferably, the brain concentration of 5,5-diphenyl barbituric acid is at least about 4 times greater than that provided by oral administration of the same amount of a free acid form of 5,5-diphenyl barbituric acid.

Preferably, the sodium 5,5-diphenyl barbiturate is administered to provide a brain concentration of 5,5-diphenyl barbituric acid of at least about 20 μg/g at 24 hours after the administration. More preferably, the sodium 5,5-diphenyl barbiturate is administered to provide a brain concentration of 5,5-diphenyl barbituric acid of at least about 20 μg/g at 36 hours after the administration. More preferably, the sodium 5,5-diphenyl barbiturate is administered to provide a brain concentration of 5,5-diphenyl barbituric acid of at least about 8 μg/g at 48 hours after the administration.

Preferably, the oral dosage form is a tablet, pill, capsule, caplet, powder, granule, suspension, gel or soft gel. More preferably, the oral dosage form is a solid form such as a tablet, pill, capsule, or caplet.

Preferably, the sodium 5,5-diphenyl barbiturate administered is at a dosage from about 0.5 mg/kg to about 100 mg/kg. More preferably, the sodium 5,5-diphenyl barbiturate administered is at a dosage from about 2 mg/kg to about 25 mg/kg. More preferably, the sodium 5,5-diphenyl barbiturate administered is at a dosage of about 3 mg/kg to about 15 mg/kg. More preferably, the sodium 5,5-diphenyl barbiturate administered is at a dosage from about 5 mg/kg to about 10 mg/kg.

Preferably, the sodium 5,5-diphenyl barbiturate is administered in the amount of from about 30 mg to about 3,000 mg per day in a 60 kg patient. More preferably, the sodium 5,5-diphenyl barbiturate is administered in the amount of from 60 mg to about 1,500 mg per day. More preferably, the sodium 5,5-diphenyl barbiturate is administered in the amount of about 150 mg to 900 mg per day. More preferably, the sodium 5,5-diphenyl barbiturate is administered in the amount of about 300 mg to 600 mg per day.

Preferably, the neurological condition is selected from the group consisting of convulsion, epilepsy, brain ischemia, traumatic brain injury, stroke, spinal cord injury, anxiety, nervous strain and movement disorders. Preferably, the movement disorder is essential tremor, dystonia or Parkinson's disease. Preferably, the movement disorder is selected from the group consisting of tremor, dystonia, chorea, athetosis, blepharospasm, hemiballysmus, myoclonus, torticollis, and writer's cramp. Preferably, the mammal is a dog, rat, mouse, primate, livestock or a pet. Preferably, the mammal is a dog. More preferably, the mammal is a human.

Accordingly, the present invention provides an oral dosage form comprising a salt form of 5,5-diphenyl barbituric acid and a pharmaceutically acceptable excipient, said salt form of 5,5-diphenyl barbituric acid is at least one salt selected from the group consisting of sodium 5,5-diphenyl barbiturate, potassium 5,5-diphenyl barbiturate and lithium 5,5-diphenyl barbiturate. Preferably, the salt form of 5,5-diphenyl barbituric acid is sodium 5,5-diphenyl barbiturate. More preferably, the oral dosage form is selected from the group consisting of a tablet, pill, capsule, caplet, powder, granule, suspension, gel and soft gel.

Accordingly, the present invention provides a method of preparing a pharmaceutical composition containing a salt form of 5,5-diphenyl barbituric acid, comprising the steps of: a) combining 5,5-diphenyl barbituric acid with an organic solvent and a base to form a salt of 5,5-diphenyl barbituric acid; and b) isolating the salt of 5,5-diphenyl barbituric acid. Preferably, the base is combined in ethanol. Preferably, the steps further comprise dissolving the base in a second solvent and adding the base in solution to a solution of 5,5-diphenyl barbituric acid in organic solvent.

Accordingly, the present invention provides a method for preparing a salt form of 5,5-diphenyl barbituric acid, comprising the steps of:
a) dissolving 5,5-diphenyl barbituric acid in an organic solvent selected from the group consisting of tetrahydrofuran, 2-methyl-tetrahydrofuran, diethyl ether, diisopropyl ether, tert-butyl methyl ether, dimethoxyethane, dioxane, diethylene glycol dimethyl ether, benzene, toluene, xylene, chlorobenzene, dichlorobenzene, ethanol, n-propyl alcohol, ethylene glycol, 1,3-butanediol, ethylene glycol monomethyl ether, N,N-dimethylformamide, N,N-dimethylacetamide, N-methylpyrrolidone, N,N-dimethylimidazoline, dimethylsulfoxide, sulfolane, acetonitrile and combinations thereof;

b) adding a base to the organic solvent, said base is at least one base selected from the group consisting of sodium hydroxide, potassium hydroxide and lithium hydroxide to the dissolved 5,5-diphenyl barbituric acid solution to form a salt form of 5,5-diphenyl barbituric acid; and c) isolating the salt form of 5,5-diphenyl barbituric acid.

Preferably, the organic solvent is tetrahydrofuran. Preferably, the base and the dissolved 5,5-diphenyl barbituric acid in step b) are present at a molar ratio of about 1:1. Preferably, the isolating step is performed by filtration. Preferably, the present invention further comprises the step of washing the isolated salt form of 5,5-diphenyl barbituric acid. Preferably, the isolated salt form is sodium 5,5-diphenyl barbiturate.

The salt form of DPB may be mono-substituted, with approximately equimolar ratios of the cation and anion. It may be substantially pure, and solid.

Figure 1:
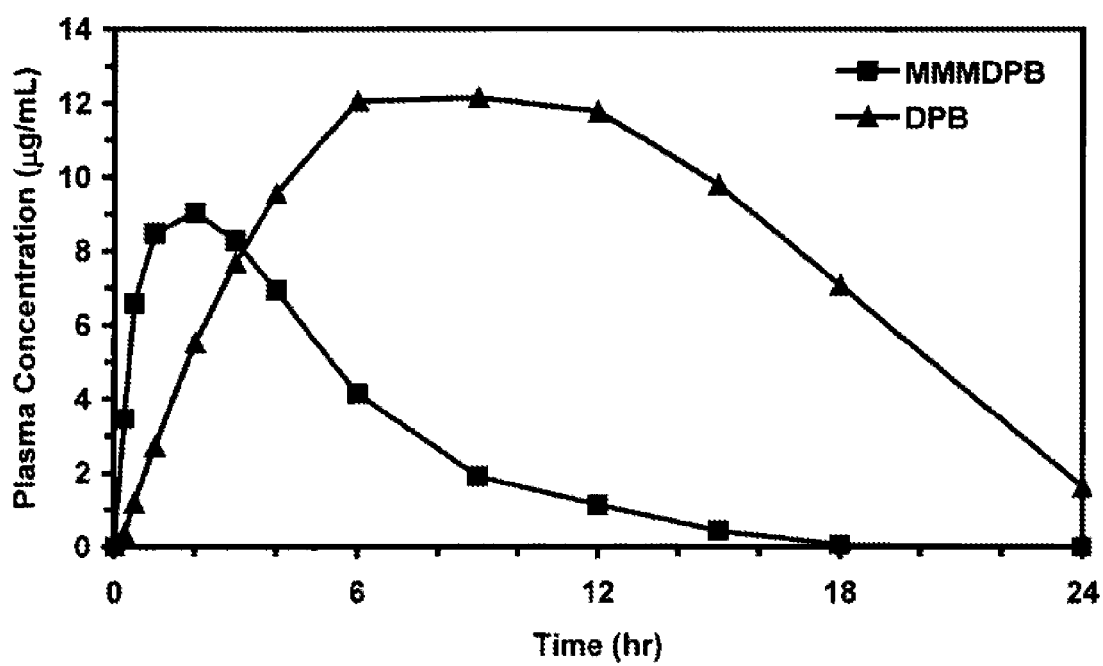
FIG. 1 illustrates the mean plasma concentrations of MMMDPB and DPB after single oral doses of MMMDPB in Beagle dogs (30 mg/kg, n=8)

The following detailed description, and the drawings to which it refers, are provided for the purpose of describing and illustrating certain examples or embodiments of the invention only and are not intended to exhaustively describe or show all possible embodiments or examples of the invention.

DETAILED DESCRIPTION OF THE INVENTION

Definitions: "DMMDPB"; is 1,3-dimethoxymethyl-5,5-diphenyl barbituric acid; "MMMDPB" is monomethoxymethyl-5,5-diphenyl barbituric acid; "DPB" is 5,5-diphenyl barbituric acid. For the purposes of the present invention "bioavailability" of a drug is defined as both the relative amount of drug from an administered dosage form which enters the systemic circulation and the rate at which the drug appears in the blood stream. Bioavailability is largely reflected by AUC, which is governed by at least 3 factors: i) absorption which controls bioavailability, followed by ii) its tissue re-distribution and iii) elimination (metabolic degradation plus renal and other mechanisms); "absolute bioavailability" is the extent or fraction of drug absorbed upon extravascular administration in comparison to the dose size administered. "Absolute bioavailability" is estimated by taking into consideration tissue re-distribution and biotransformation (i.e., elimination) which can be estimated in turn via intravenous administration of the drug. "Improved bioavailability" refers to a higher AUC for salts of DPB as compared to that of free acid forms of DPB (assuming the metabolism and tissue distribution is relatively unchanged). Preferably, an improved bioavailability refers to a $AUC_{0-t}$ of 5,5-diphenyl barbituric acid of at least 800 µg·hr/mL. "AUC" refers to the mean area under the plasma concentration-time curve; "$AUC_{0-t}$" refers to area under the concentration-time curve from time zero to the time of the last sample collection; "$AUC_{0-24}$" refers to area under the concentration-time curve from time zero to 24 hours; "$AUC_{0-48}$" refers to area under the concentration-time curve from time zero to 48 hours; "$C_{max}$" refers to maximum observed plasma concentration; "$T_{max}$" (or "$t_{max}$") refers to the time to achieve the $C_{max}$; "$t_{1/2}$" refers to the apparent half-life and is calculated as ($\ln 2/K_{el}$), where $K_{el}$ refers to the apparent first-order elimination rate constant. "NaDPB" and "sodium salt of DPB" are used herein interchangeably, and refer to sodium 5,5-diphenyl barbiturate; "NaMMMDPB" and sodium salt of MMMDPB are used herein interchangeably and refer to sodium monomethoxymethyl-5,5-diphenyl barbiturate. Unless otherwise indicated, "mean plasma concentration" and "plasma concentration" are used herein interchangeably; "mean brain concentration" and "brain concentration" are used herein interchangeably; "BQL" refers to below quantitation limit of assay; "T" refers to the intravenous infusion time (in minutes) of a drug; "HPLC" refers to high performance liquid chromatography; "pharmaceutically acceptable" refers to physiologically tolerable materials, which do not typically produce an allergic or other untoward reaction, such as gastric upset, dizziness and the like, when administered to a mammal; "mammal" refers to a class of higher vertebrates comprising man and all other animals that nourish their young with milk secreted by mammary glands and have the skin usually more or less covered with hair; and "treating" is intended to encompass relieving, alleviating or eliminating at least one symptom of a neurological condition in a mammal.

The present invention succeeds where previous efforts to deliver optimal blood levels of DPB have failed. The present invention solves the major bioavailability problems associated with the poorly dissolved non-sedating barbiturate drug (i.e., DPB). The present invention provides a salt form of DPB that provides sufficient blood levels to produce clinically meaningful improvements in neurological conditions.

The present invention provides a method of preparing and isolating various salt forms of DPB. Salts of DPB in the present invention include at least one compound selected from the group consisting of sodium DPB, potassium DPB and lithium DPB. Other pharmaceutically acceptable salts of DPB are also suitable for practicing the present invention.

The present inventors have unexpectedly discovered a novel method for delivering DPB to a patient in need of treatment for a neurological condition, comprising the step of administering an isolated salt form of DPB in an oral dosage form; preferably, the oral dosage form comprises sodium 5,5-diphenyl barbiturate. The present composition and method offer significant clinical advantages over the prior art in that it provides an improved bioavailability and enhanced delivery of DPB to the central nervous system.

Aside from allowing infrequent administration (which can significantly improve patient compliance with the drug), the present invention provides a dosage form of DPB salts having an improved bioavailability that can significantly increase the reliability of each dose of the drug. The present invention also ensures maintenance of optimal serum and tissue levels of DPB crucial for its therapeutic effectiveness. Accordingly, the benefits of a higher effective bioavailability include lower dose, fewer pills (e.g., one a day) with improved compliance, reliability and predictability of therapy.

The advantageous bioavailability of DPB salts results from an increased rate and extent of absorption as measured by AUC and $C_{max}$ over a defined period of time (e.g., 8, 12, 24, 36 and 48 hours). Without intending to be limited, it is presumed that the processes of tissue re-distribution and biotransformation (e.g., metabolism) and excretion are probably about the same for DPB (free acid) as for the salt forms of DPB, and that the advantages of the salt forms derive primarily from the fast absorption. For example, a higher $C_{max}$ may drive a higher brain level of DPB. On the other hand, it is possible that the metal anion (e.g., sodium) remains with the DPB moiety in the mammal, in which case the post-absorption pharmacological phenomena also play a role in higher effective bioavailability.

The present invention is surprising in light of the observation that salts of other barbiturates such as pentobarbital, while altering the rate of absorption, do not share this unique property of improving bioavailability. (See, *The Pharmacological Basis of Therapeutics* 2001, p. 417, Tenth Ed.)

Bioavailability Studies

The present invention represents a surprising finding that a dosage form of DPB salts exhibits an improved bioavailability over its free acid counterpart. Without wishing to be bound by a theory, it is believed that the improved bioavailability is at least in part attributable to an increase in DPB absorption, ultimately leading to an increase the serum level of DPB. Improved bioavailability of a drug is often reflected by an increase in an AUC (concentration-time curve). In some incidence, an improved bioavailability may also be reflected by an increase in $C_{max}$.

Calculations of AUC and $C_{max}$

In accordance with the present invention, pharmacokinetic parameters were calculated using standard non-compartmental methods, as implemented in WinNonlin™ 4.0.1. The mean, standard deviation (SD) and percent coefficient (CV (%)) of variations were calculated for plasma concentrations of MMMDPB and DPB for each sampling time and for each treatment. The mean, SD and CV (%) were used to calculate the $AUC_{0-t}$ (µg·h/mL), $C_{max}$ (µg/ml) (the maximum observed concentration), $T_{max}$ (hours) (the time to reach that peak concentration) and $K_{el}$ (the elimination rate constant) for each animal and each analyte.

Areas under the concentration-time curves (AUC) were determined with respect to each animal that received oral administration of either NaDPB, NaMMMDPB or their free acid counterparts. $AUC_{0-t}$ was calculated using the linear trapezoidal rule, which employs an approximate integration formula. The area of each trapezoid was calculated, and the sum of all the areas of all the trapezoids yielded an estimate of the true area under the curve. (See, Gibaldi et al. Pharmacokinetics. $2^{nd}$ Ed. Marcel Dekker, Inc., 1982; Yeh et al., A comparison of numerical integrating algorithms by trapezoidal, lagrange, and spline approximations. *J. Pharmacokinet Biopharm.* 6: 79 (1978), the disclosure of which is herein incorporated by reference.) $C_{max}$ and $T_{max}$ were then determined for each concentration vs. time profile. Elimination rate constant ($K_{el}$) was calculated using regression analyses on the natural log (ln) of plasma concentration values (y) versus time (x).

Pharmacokinetic Profile

As noted above, the present invention resides in the discovery that a salt form of DPB has an improved pharmacokinetic profile that can simultaneously accomplish two results. First, the oral dosage form containing a salt form of DPB maintains therapeutic levels of the DPB over a time period of (e.g., over 48-hour) after dosing. Second, the oral dosage form containing a salt form of DPB results in optimal delivery of DPB to blood and to the central nervous system (e.g., brain) where neurological benefits occur.

In order to obtain these benefits, it is necessary to prepare a salt form of DPB as an oral dosage form of DPB to achieve certain pharmacokinetic parameters, when compared to the oral dosage form of the corresponding free acid form of DPB. The oral dosage form of the salt form of DPB, in particular the sodium 5,5-diphenyl barbiturate, significantly improves the bioavailability by increasing the blood levels of DPB and the blood level versus time profile (e.g., $AUC_{0-t}$ and $C_{max}$) for DPB. In addition to increasing the peak DPB blood levels (i.e., $C_{max}$), it is important that the total amount of DPB absorbed (total drug absorption is referred to as AUC or area under the curve) be increased for the oral dosage form of the salt form of DPB as well.

AUC for the oral dosage form of a salt form of 5,5-diphenyl barbituric acid (such as sodium 5,5-diphenyl barbiturate) increase to at least about 1.5 fold greater, when compared to that for the oral dosage form of the free acid form of 5,5-diphenyl barbituric acid. All of the AUCs over 24-hour, 36-hour and 48-hour intervals exhibit an increase for the oral dosage form of the salt form of 5,5-diphenyl barbituric acid. Preferably, the oral dosage form contains sufficient amount of the salt form of 5,5-diphenyl barbituric acid that provides AUC of at least about 2 fold greater, when compared to that for the oral dosage form of the free acid form of 5,5-diphenyl barbituric acid. More preferably, the oral dosage form contains sufficient amount of the salt form of 5,5-diphenyl barbituric acid that provides AUC of at least about 2.5 fold greater, when compared to that for the oral dosage form of the free acid form of 5,5-diphenyl barbituric acid. More preferably, the oral dosage form contains sufficient amount of the salt form of 5,5-diphenyl barbituric acid that provides AUC of at least about 3 fold greater, when compared to that for the oral dosage form of the free acid form of 5,5-diphenyl barbituric acid. More preferably, the oral dosage form contains sufficient amount of the salt form of 5,5-diphenyl barbituric acid that provides AUC of at least about 3.5 fold greater, when compared to that for the oral dosage form of the free acid form of 5,5-diphenyl barbituric acid. Thus, with respect to the extent of absorption, the oral dosage form of a salt form of 5,5-diphenyl barbituric acid of this invention should be considered improved bioavailability for DPB.

$C_{max}$ for the oral dosage form of a salt form of 5,5-diphenyl barbituric acid (such as sodium 5,5-diphenyl barbiturate) increases at least about 1.5 fold greater, when compared to that for the oral dosage form of the free acid form of 5,5-diphenyl barbituric acid. All of the plasma concentrations over 24-hour, 36-hour and 48-hour intervals exhibit an increase for the oral dosage form of the salt form of 5,5-diphenyl barbituric acid. More preferably, the oral dosage form contains sufficient amount of the salt form of 5,5-diphenyl barbituric acid that provides $C_{max}$ of at least about 2 fold greater, when compared to that for the oral dosage form of the free acid form of 5,5-diphenyl barbituric acid. More preferably, the oral dosage form contains sufficient amount of the salt form of 5,5-diphenyl barbituric acid that provides $C_{max}$ of at least about 2.5 fold greater, when compared to that for the oral dosage form of the free acid form of 5,5-diphenyl barbituric acid. More preferably, the oral dosage form contains sufficient amount of the salt form of 5,5-diphenyl barbituric acid that provides $C_{max}$ of at least about 3 fold greater, when compared to that for the oral dosage form of the free acid form of 5,5-diphenyl barbituric acid. Thus, with respect to the peak plasma concentration, the oral dosage form of a salt form of 5,5-diphenyl barbituric acid of this invention should be considered as producing improved bioavailability for DPB.

An improvement in oral bioavailability of DPB is believed to be critical in maintaining its therapeutic efficacy, which is reflected by an optimal AUC. An optimal $C_{max}$ may further reflect the improved oral bioavailability of DPB. Adequate delivery of DPB to the central nervous system is believed to play a significant role in its effects on the central nervous system in neurological conditions in patients. It is contemplated that a plasma level of at least about 0.5 µg/ml is desirable. More preferably, it is contemplated that an optimal plasma level may be about 10 µg/ml to about 125 µg/ml of DPB. More preferably, it is contemplated that an optimal plasma level may be about 15 µg/ml to about 75 µg/ml of DPB.

It is noted that an oral dosage form comprising a sodium salt of MMMDPB does not increase bioavailability of DPB. The $AUC_{0-t}$ and $C_{max}$ of DPB were in fact lower after oral administration of the sodium salt form of MMMDPB, as compared to the oral administration of the free acid form of MMMDPB (135.10 µg·hr/mL vs. 193.18 µg·hr/mL and 7.28 µg/mL vs. 9.39 µg/mL, respectively) (See, Table 1). Accordingly, the sodium salt form of MMMDPB fails to increase the bioavailability of DPB.

Preferably, the salt form of 5,5-diphenylbarbituric acid is administered in a sufficient amount to provide a brain concentration of 5,5-diphenylbarbituric acid that is at least about 1.5 times greater than that seen after the oral administration of the same amount of a free acid form of 5,5-diphenylbarbituric acid. More preferably, the brain concentration of 5,5-diphenylbarbituric acid is at least about 2.0 times greater than that seen after the oral administration of the same amount of a free acid form of 5,5-diphenylbarbituric acid. More preferably, the brain concentration of 5,5-diphenylbarbituric acid is at least about 3 times greater than that seen after the oral administration of the same amount of a free acid form of 5,5-diphenylbarbituric acid. More preferably, the brain concentration of 5,5-diphenylbarbituric acid is at least about 4 times greater than that seen after the oral administration of the same amount of a free acid form of 5,5-diphenylbarbituric acid.

The present oral dosage form of a salt form of DPB provides an optimal delivery of DPB to the central nervous system (e.g., brain). Preferably, administration of a single oral dose of sodium 5,5-diphenyl barbiturate permits a brain concentration of at least about 20 µg/g of DPB 24 hours after the administration. Preferably, administration of a single oral dose of sodium 5,5-diphenyl barbiturate permits a brain concentration of at least about 20 µg/g of DPB 36 hours after the administration. Preferably, administration of a single oral dose of sodium 5,5-diphenyl barbiturate permits a brain concentration of at least about 8 µg/g of DPB 48 hours after the administration.

Based on cumulative observations from animal studies using maximal electroshock seizure (MES) test (See, for example, *Epilepsia* 1975, 16:575-581), it is generally believed that brain concentrations of DPB less than 1 μg/ml are usually ineffective or marginally effective (approximately 20% or less protection); brain concentrations in excess of 10 μg/ml are usually effective (50% or greater protection); and brain concentrations of 1-10 μg/ml were variably effective (between 30 and 40% protection). Accordingly, the present oral dosage form of a salt form of DPB can sufficiently provide effective amounts of DPB to the brains where it exerts its pharmacological effects (such as anticonvulsant and neuroprotection).

Without wishing to be bound by any theory, it is believed that the sodium salt of DPB is better absorbed more rapidly and completely from the intestines. It is further believed that the resulting higher plasma concentration of DPB leads to a quicker drug entry into the central nervous system.

In general, orally administered medicines are preferred for ease of use, cost efficiency and patient compliance. However, oral ingestion often fails to yield effective plasma levels with many hydrophobic drugs, due to failure of absorption. Moreover, this route of administration may be problematic when drugs absorbed from the gastrointestinal tract are extensively metabolized by the liver before they gain access to the general circulation. We surprisingly found that a salt form of DPB (i.e., sodium 5,5-diphenyl barbiturate) is better in achieving plasma concentrations of DPB so as to deliver an optimal plasma concentration of DPB. The increased plasma levels with oral administration of sodium salt of DPB are parallel to that of intravenous administration. Infusion of drugs, however, has its disadvantages. Trained personnel are needed. Rate of administration may be critical and requires careful adjustment and monitoring. Strict sepsis must be maintained to avoid infection, pain may accompany the injection, and it is usually more expensive and less safe than oral medication.

Figure 5:
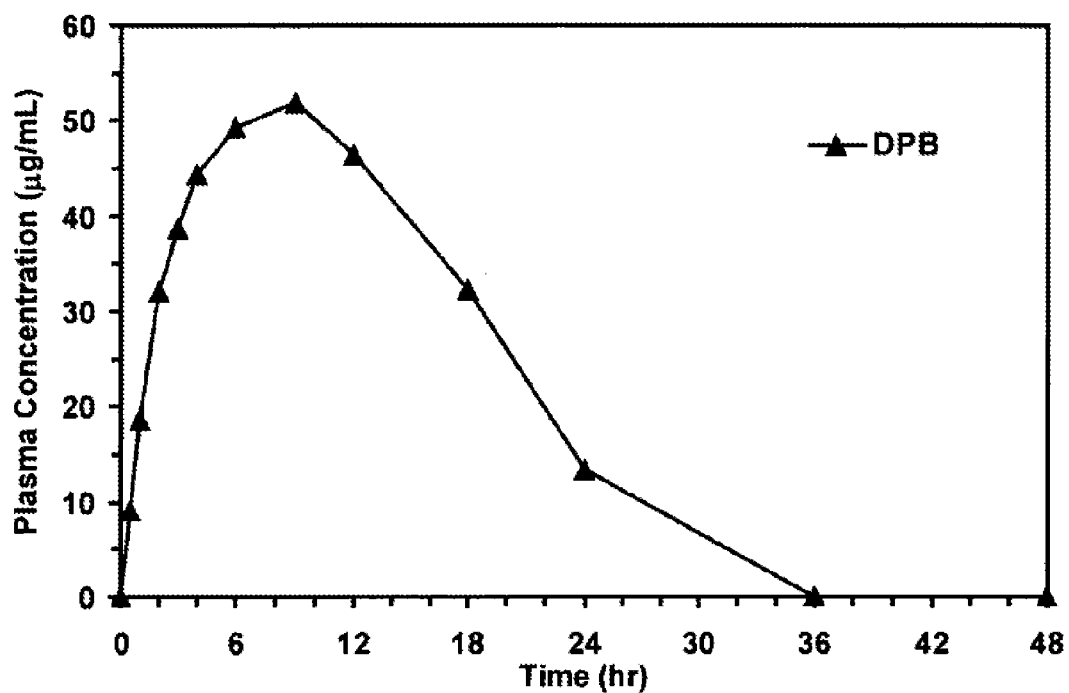
FIG. 5 illustrates the mean plasma concentrations of DPB after single oral doses of NaDPB in Beagle dogs (75 mg/kg, n=8)

It is observed that the pharmacokinetic parameters $AUC_{0-t}$ and $C_{max}$ are greater in female rats when compared to in male rats for DPB as well as all of the other non-sedating barbiturates tested (See, Table 3 and FIG. 5). We observed that administration of the salt form of DPB reduces variability of the plasma levels between female and male rats. The observation is unexpected and surprising. To the best of the inventors' knowledge, there has been no report regarding a salt of barbiturate that may reduce the differences in serum barbiturates between males and females, let alone the non-sedating barbiturates. Without wishing to be bound by a theory, the present unexpected findings are consistent with the hypothesis that the salt forms of DPB can lead to a better absorption of DPB, and thus reduce the variability between the two sexes.

In accordance with the present invention, the present invention provides a method of delivering a barbituric acid derivative (i.e., DPB) to the central nervous system including the brain. In mammals, brain keeps its environment constant by a blood-brain barrier. The blood-brain barrier separates the brain from the blood circulation and is involved in the homeostasis of the brain. The blood-brain barrier and the blood-cerebrospinal fluid barrier often preclude or slow the entrance of drugs into the central nervous system. The blood-brain barrier is composed of various cell types like endothelial cells, astrocytes, microglial cells, perivascular macrophages, and pericytes. The cerebral and endothelial cells form the morphological and functional basis of the blood-brain barrier. The bulk of the brain and the spinal cord is surrounded by a specially secreted clear fluid called the cerebrospinal fluid. Drug substances need to move across the blood-brain barrier before they can find their way into the cerebrospinal fluid where they are free to diffuse into the tissues of the brain. The entry of drugs such as barbituric acid derivatives into the central nervous system is restricted by the blood-brain barrier. We surprisingly found that oral administration of the sodium salt form of DPB enhances bioavailability and enables the DPB to enter readily into the central nervous system as evidenced by the appearance in the brain. It is believed that the higher rate and extent of delivery of DPB into the central nervous system provides a rapid and effective treatment for neurological conditions by this class of non-sedating barbituric acid derivatives.

The present invention is directed to a method of treating neurological conditions in a mammal. For purposes of the present invention, the mammal encompasses rodents (such as rats), dogs, human etc. Preferably, the mammal is a human. More particularly, the present invention provides a method of treating neurological deficits in a patient by providing an improved bioavailability with an effective amount of DPB. According to the present invention, the term "patient" will encompass any mammal requiring treatment with DPB, particularly a human patient suffering from a neurological disorder.

For the purpose of the present invention, neurological conditions include, but are not limited to, convulsion, seizure, epilepsy, brain ischemia, traumatic brain injury, stroke, spinal cord injury, anxiety, nervous strain, and movement disorders. Movement disorders include a wide variety of disease states and physiological conditions. Non-limiting examples include various dyskinesias such as tremor, dystonia, chorea, athetosis, blepharospasm, as well as hemiballysmus, myoclonus, and focal dystonias, such as writer's cramp and torticollis. These abnormal involuntary movements may vary significantly in rate, frequency, periodicity and progression. Such movements may be seen in sometimes overlapping disorders such as Parkinson's disease; essential tremor, a.k.a. benign tremor or familial tremor; tic disorders, e.g., Tourette's syndrome; idiopathic dystonia (inducing writer's cramp), progressive supranuclear palsy and Wilson's disease. Essential tremor is one of the most common forms of tremor and of all movement disorders and it affects approximately 1-22% of elder populations. Parkinson's disease is a progressive disorder with a prevalence of 1-2% in people over the age of 50. Preferably, the neurological condition is brain ischemia, epilepsy, essential tremor, or Parkinson's disease.

The dosage for the salt form of DPB or pharmaceutically acceptable salts thereof in the compositions of the invention will vary depending on several factors, including, but not limited to, the age, weight, and species of the patient, the general health of the patient, the severity of the symptoms in neurological injury, whether the composition is being administered alone or in combination with other agents, the incidence of side effects and the like.

While it is possible for the salt form of DPB to be administered alone, it is preferably present as a pharmaceutical composition. Preferably, the compositions of the present invention comprise at least one sodium salt of DPB, as defined above, together with one or more acceptable carriers thereof and optionally other therapeutic agents.

The above-mentioned method may be practiced by administration of the compound itself (e.g., salt form of DPB) in a combination with other active ingredients in a pharmaceutical composition. Other therapeutic agents suitable for use herein are any compatible drugs that are effective by the same or other mechanisms for the intended purpose, or drugs that are complementary to those of the present agents, e.g., other barbituric acid derivatives, particularly MMMDPB, DMMDPB or other non-sedative barbiturates. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the dose upward until optimal results are obtained. The therapeutic method of the invention may be used in conjunction with other therapies as determined by the practitioner without undue experimentation.

Pharmaceutical Composition Comprising Sodium, Potassium, and Lithium Salts of DPB The present invention encompasses a pharmaceutical composition, a pharmaceutical dosage form, a kit, and a method of treating a neurological condition using a salt form of DPB. The pharmaceutical composition of the present invention comprises a salt form of DPB and a pharmaceutically acceptable excipient. Preferably, the pharmaceutical composition comprises an isolated salt of DPB. Preferably, the salt form is sodium salt, potassium salt, lithium salt or the like. More preferably, the salt form is a sodium salt form of DPB.

The pharmaceutical composition of the present invention can be administered orally in the form of dry oral dosage forms. In accordance with the present invention, the salt form of DPB may be formulated into a variety of pharmaceutical compositions and dosage forms for therapeutic uses, especially in the treatment of a neurological condition. The pharmaceutical composition of the present invention can be administered orally in the form of tablets, pills, capsules, caplets, powders, granules, suspension, gels and the like. Oral compositions can include standard vehicles, excipients, and diluents. The oral dosage forms of the present pharmaceutical composition can be prepared by techniques known in the art and contains a therapeutically effective amount of an isolated salt form of DPB. A therapeutically effective oral dosage for formulations of the invention is determined by standard clinical techniques according to the judgment of a medical practitioner. For example, in addition to information provided in medical reference books and pharmaceutical literature, well-known in vitro or in vivo assays can be used to help identify optimal dosages.

The pharmaceutical compositions of the present invention may be used alone or under appropriate situations, in combination with, other pharmaceutically-active compounds. For example, other sedating barbiturates may be used in combination.

Pharmaceutical compositions of the present invention may contain one or more pharmaceutically acceptable excipients. Excipients are added to the composition for a variety of purposes. The compositions may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art (See, *Remington's Pharmaceutical Sciences*, 19th Edition, Alfonso R. Gennaro ed., Mack Publishing Company, Easton, Pa., Eighteenth edition (1995), the disclosure of which is incorporated by reference).

Preferably, the pharmaceutical composition is a dry oral dosage form. Preferably, the pharmaceutical composition is a solid dosage form. Preferably, the pharmaceutical composition is an oral dosage form selected from the group consisting of tablet, pill, capsule, caplet, powder, and granule. Dry dosage forms may include pharmaceutically acceptable additives, such as excipients, carriers, diluents, stabilizers, plasticizers, binders, glidants, disintegrants, bulking agents, lubricants, plasticizers, colorants, film formers, flavoring agents, preservatives, dosing vehicles, and any combination of any of the foregoing.

The present pharmaceutical composition can be provided in unit dosage form, wherein each dosage unit, e.g., a tablet or capsule, contains predetermined amount of the drug, alone or in combination other pharmaceutically-active agents. The term "unit dosage form" refers to physically discrete units suitable as unitary dosages for human and animal subjects, each unit containing a predetermined quantity of the composition of the present invention, alone or in combination with other pharmaceutically-active agents, calculated in an amount sufficient to produce the desired effect, in association with a pharmaceutically acceptable excipient (e.g., saline). The specifications for the novel unit dosage forms of the present invention depend on the particular effects to be achieved and the drug's particular pharmacokinetic parameters in the particular hosts.

Tablets and pills can additionally be prepared with enteric coatings and other release-controlling coatings so long as it provides a similar pharmacokinetic profile. The coating may be colored with a pharmaceutically accepted dye. The amount of dye and other excipients in the coating liquid may vary and will not impact on the tablets or pills. The coating liquid generally comprises film-forming polymers such as hydroxypropyl cellulose, hydroxypropylmethyl cellulose, cellulose ester or ether, in acrylic polymer or a mixture of polymers. The coating solution is generally an aqueous solution that may further comprising propylene glycol, sorbitan monoleate, sorbic acid, fillers and/or colorants such as titanium dioxide, a pharmaceutically acceptable pigment.

Diluents increase the bulk of a solid pharmaceutical composition and may make a pharmaceutical dosage form containing the composition easier to manufacture and for the patient and caregiver to handle. Diluents for solid compositions include, for example, microcrystalline cellulose (e.g. AVICEL®), polymer (e.g., hydroxypropylmethyl cellulose) microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl famarate, stearic acid, talc and zinc stearate. Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid. Orally administered formulations of the invention may also optionally include one or more sweetening agents and one or more flavoring agents to provide a pharmaceutically palatable preparation. Compositions may further be colored using any pharmaceutically acceptable colorant to improve their appearance and/or facilitate patient identification of the product and unit dosage level.

Selection of excipients and the amounts to use may be readily determined by formulation scientists based upon experience and consideration of standard procedures and reference works in the field. The solid compositions of the present invention include powders, granulates, aggregates and compacted compositions. The preferred route of the present invention is oral. The dosages may be conveniently presented in unit dosage form and prepared by any of the methods well-known in the pharmaceutical arts. Dosage forms include solid dosage forms like tablets, pills, powders, caplets, granules, capsules, sachets, troches and lozenges. An especially preferred dosage form of the present invention is a tablet.

The magnitude of a prophylactic or therapeutic dose of the salt forms of DPB in the treatment of a neurological condition is typically vary with the severity and type of neurological condition. The dose, and perhaps the dose frequency, may also vary according to age, body weight, response, and the past medical history of the patient. Suitable dosing regimens can be readily selected by those skilled in the art with due consideration of such factors by following, for example, dosages reported in the literature and recommended in the Physician's Desk Reference®.

In one embodiment of the invention, the salt form of DPB (e.g., NaDPB) is administered orally in a single dose. Preferably, the sodium 5,5-diphenyl barbiturate is administered orally at a dosage from about 0.5 mg/kg to about 100 mg/kg. More preferably, the sodium 5,5-diphenyl barbiturate is administered orally at a dosage from about 2 mg/kg to about 25 mg/kg. More preferably, the sodium 5,5-diphenyl barbiturate is administered orally at a dosage of about 3 mg/kg to about 15 mg/kg. More preferably, the sodium 5,5-diphenyl barbiturate is administered orally at a dosage of about 5 mg/kg to about 10 mg/kg.

Preferably, the sodium 5,5-diphenyl barbiturate is administered in the amount of from about 30 mg to about 3,000 mg per day in a 60 kg patient. More preferably, the sodium 5,5-diphenyl barbiturate is administered orally in the amount of from 60 mg to about 1,500 mg per day. More preferably, the sodium 5,5-diphenyl barbiturate is administered orally in the amount of about 150 mg to 900 mg per day. More preferably, the sodium 5,5-diphenyl barbiturate is administered orally in the amount of about 300 mg to 600 mg per day.

In another embodiment of the invention, the salt form of DPB is administered orally and daily in an amount of from about 1 to about 2,000 mg, preferably from about 50 to about 1,000 mg, more preferably from about 100 to 750 mg, and most preferably from about 200 to about 500 mg.

The present invention encompasses a method of treating a neurological condition with therapeutically safe and effective doses of DPB. Consequently, in another embodiment of the invention, a salt form of DPB is administered daily in a cycle of about one week (e.g., once a day consecutively for one week). In yet another embodiment of the invention, a salt form of DPB is administered daily in a cycle of about 2 weeks (e.g., once a day consecutively for two weeks). The invention further allows the frequency, number, and length of DPB salts dosing cycles to be increased. In yet another embodiment of the invention, DPB salts are administered for a greater number of daily doses as well as cycles that would typically be sufficient to treat the underlying neurological condition.

The dosage amounts and frequencies provided above are encompassed by the terms "therapeutically effective," "prophylactically effective," and "therapeutically or prophylactically effective" as used herein. When used in connection with an amount of DPB salts, these terms further encompass an amount of DPB salts that reduce, prevent, or eliminate an adverse effect associated with the underlying neurological condition.

According to the invention, the absolute bioavailability of DPB upon oral administration of a DPB salt, as measured by the AUC at a given time for the orally administered DPB salt as compared to intravenous (IV) administration, is at least about 55%, 65%, 75%, or 85%.

The pharmaceutical composition of the present invention may be administered to a fasted human. The present composition may also be administered to a human after meals.

The present invention encompasses a kit that simplifies the administration of appropriate amounts of the salt forms of DPB to a patient. A typical kit of the present invention comprises a dosage form of an isolated salt form of DPB, and a pharmaceutically acceptable excipient.

In an embodiment, the present invention provides a method of preparing a pharmaceutical composition containing a salt form of 5,5-diphenyl barbituric acid, comprising the steps of: a) combining 5,5-diphenyl barbituric acid with an organic solvent and a base to form a salt of 5,5-diphenyl barbituric acid; and b) isolating the salt of 5,5-diphenyl barbituric acid.

In another embodiment, the present invention provides a method for preparing a pharmaceutical composition comprising the steps of: a) dissolving 5,5-diphenyl barbituric acid in an organic solvent selected from the group consisting of tetrahydrofuran, 2-methyl-tetrahydrofuran, diethyl ether, diisopropyl ether, tert-butyl methyl ether, dimethoxyethane, dioxane, diethylene glycol dimethyl ether, benzene, toluene, xylene, chlorobenzene, dichlorobenzene, ethanol, n-propyl alcohol, ethylene glycol, 1,3-butanediol, ethylene glycol monomethyl ether, N,N-dimethylformamide, N,N-dimethylacetamide, N-methylpyrrolidone, N,N-dimethylimidazoline, dimethylsulfoxide, sulfolane, acetonitrile and combination thereof; b) adding a basic solution to the organic solvent, said base is at least one base selected from the group consisting of sodium hydroxide solution, potassium hydroxide solution and lithium hydroxide solution to the dissolved 5,5-diphenyl barbituric acid solution to form a salt of 5,5-diphenyl barbituric acid; and c) isolating the salt of 5,5-diphenyl barbituric acid. Preferably, the salt is a sodium salt of 5,5-diphenyl barbituric acid.

The dissolution step of 5,5-diphenyl barbituric acid may be carried out in various solvents. Examples of solvents used include ethers such as tetrahydrofuran (THF), 2-methyl-tetrahydrofuran, dimethoxyethane, dioxane and diethylene glycol dimethyl ether; aromatic hydrocarbons such as benzene, toluene, xylene, chlorobenzene and dichlorobenzene; alcohols such as ethanol, n-propyl alcohol, ethylene glycol, 1,3-butanediol and ethylene glycol monomethyl ether; amides such as N,N-dimethylformamide, N,N-dimethylacetamide, N-methylpyrrolidone and N,N-dimethylimidazoline; hydrocarbons containing sulfur such as dimethylsulfoxide and sulfolane, and water; or polar aprotic solvents such as acetonitrile and the like. Preferably, the organic solvent is tetrahydrofuran.

In the above reaction, approximately a 1:1 molar ratio of a 5,5-diphenyl barbituric acid and a base is used. The reaction is carried out at a temperature that will be adjusted by a person skilled in the art to the base used and to the solvent used.

The isolating step may be performed by filtering. Other convenient methods may be adopted by one skilled in the art. Optionally, the precipitation may be enhanced by stirring and cooling. Preferably, the solution is cooled to about 4° C. Preferably, the solution is stirred for about 2 hours at room temperature followed by cooling to 4° C. Preferably, the present invention further comprises the step of washing the isolated salt of 5,5-diphenyl barbituric acid.

The purity of the DPB salt is at least about 90%. The purity may be at least about 95%, 97%, or 99%. In this context, purity refers to the proportion of DPB salt divided by the total of DPB salt plus free acid. A substantially pure DPB salt is one that is at least about 90% pure.

The precise amount of sodium salt of DPB administered to a patient may vary depending upon the degree of the disease and the size of the patient. A normal-weight (~60 kg) adult may be started a dosage from about 0.5 mg/kg to about 50 mg/kg. Preferably, the amount of the sodium salt of DPB is about 2 mg/kg to about 25 mg/kg. More preferably, the amount of the sodium salt of DPB is about 3 mg/kg to about 15 mg/kg. More preferably, the amount of the sodium salt of DPB is about 5 mg/kg to about 10 mg/kg. Tablets, capsules, lozenges and other dosage forms preferably contain unit dosage of sodium salt of DPB.

The daily dose of the pharmaceutical composition of this invention administered to a patient in a single dose can be in the amounts from about 30 mg to about 3,000 mg. Preferably, the daily dose is about 60 mg to about 1,500 mg. More preferably, the daily dose is about 150 mg to about 900 mg. More preferably, the daily dose is about 300 mg to about 600 mg.

An embodiment of the invention relates to a solid oral pharmaceutical dosage form comprising a salt of diphenyl barbituric acid. The invention provides a method comprising adding a base to diphenyl barbituric acid to produce a salt of DPB by base addition. The present invention relates to a method of producing a pharmaceutical product that comprises compounding a DPB salt and a vehicle to produce a solid dosage form The present invention involves a method comprising administering a DPB salt to a mammal orally in solid dosage form at a clinically acceptable dose. The dose may produce a blood plasma concentration of DPB at least about 25 µg/ml. The method of administration produces a therapeutic effect. The dose may be effective to provide neuroprotection. An effective amount of the composition may be that which produces the desired pharmacological effect in a host.

An embodiment of the invention relates to a solid oral pharmaceutical dosage form comprising a sodium or potassium salt of diphenyl barbituric acid. A method according to the invention comprises converting DPB as free acid to the sodium or potassium salt. The present invention provides a method of producing a pharmaceutical product comprising compounding a DPB salt and a vehicle to produce a solid dosage form, wherein the salt is a sodium or potassium salt. The present invention relates to a method of treating a neurological disorder comprising administering a DPB salt to a mammal orally in solid dosage form in an amount effective to achieve a desired pharmacological effect. The disorder may be a strain or stress condition or nervous dysfunction such as convulsions, seizures, muscle stiffness, nervous strain and anxiety. The compositions may be used to treat epilepsy or as a neuroprotective agent and can be administered to individuals undergoing surgery or experiencing or having a risk of atrial fibrillation, transient ischemic attack, cerebral ischemia, head trauma, or other acute neurological injuries. The pharmaceutical compositions may be a tablet that may be coated, or a hard or soft capsule. The dose may be at least about 0.5, 1, 5, 10, or 15 mg/kg/day, and may produce a blood plasma concentration of DPB at least about 10 µg/ml.

The DPB salts of the present invention used in a solid oral pharmaceutical dosage form may be pharmaceutically acceptable salts including salts derived from an appropriate base, such as an alkali metal (for example, sodium, potassium), an alkaline earth metal (for example, calcium, magnesium), ammonium, and the like. All of these salt forms may be prepared by conventional means from the corresponding compound by reacting the appropriate base with the compound in free form. The salt forms may be combined with excipients and formed into solid dosage forms.

The present inventive compositions and methods allow for treatment of a diverse patient population (male/female, young/old) with acceptable inter-patient and intra-patient variability, substantially less than is present with DPB free acid. The present invention provides improved effective bioavailability as measured by serum DPB. The invention may provide a higher serum level (AUC and/or $C_{max}$) over a short time (~8, 12, 18, or 24 hrs) than the same dose and formulation of the free acid would provide. The method may provide the same serum level over a short time as compared to a higher dose of the free acid.

A method for achieving a target therapeutic blood level of DPB according to the present invention comprises administering isolated sodium salt of DPB. The therapeutic blood level may be measured by AUC or $C_{max}$, and is higher than the level measured for the DPB free acid. The amount of DPB salt administered to produce the target blood level of DPB may be at least about 10%, 20%, 30%, 40%, or 50% less than the amount required for DPB free acid. The amount of DPB salt required for a given blood level may be less than about ⅕, ¼, ⅓, or ½ of the amount of DPB free acid required for the same blood level.

The methods and compositions of the invention are effective to produce a blood plasma concentration of DPB of about 10-125, 25-100, or 40-80 µg/ml.

Having now generally described this invention, the same will be better understood by reference to the following Examples, which are provided herein solely for purposes of illustration only and are not intended to be limiting of the invention or any embodiment thereof, unless so specified.

EXAMPLES

Example 1

Preparation of Salt Forms of DPB Sodium Salt

Materials:

| Compound | Molecular weight | Weight (grams) | MMoles | Volumes |
|---|---|---|---|---|
| DPB | 280 | 46.35 | 166 | |
| NaOH | 40 | 6.60 | 165 | |
| THF | | | | 1,500 mL + 150 mL |
| DI water | | | | 25 mL |

THF: tetrahydrofuran;
DI water: deionized water

Procedure:

DPB was dissolved in 1,500 mL THF. The turbid solution was filtered through folded filter paper. Sodium hydroxide solution was prepared by dissolving in a mixture of 150 mL THF and 25 mL water. The sodium hydroxide solution was added drop-wise to the DPB solution over a period of 0.5 hour. The sodium salt of DPB formed and precipitated from the solution. The mixture was stirred for about 2 hours at room temperature and then cooled to 4° C. and stirred at that temperature for an additional 2 hours. The product was filtered and washed with cold THF. 42.57 grams wet product was obtained. The collected salt was dried in a vacuum oven at 50° C. to constant weight of 40.12 grams. Yield: 80%.

Potassium Salt

Materials:

| Compound | Molecular weight | Weight (grams) | MMoles | Volumes |
|---|---|---|---|---|
| DPB | 280 | 9.18 | 32.8 | |
| KOH | 56.1 | 2.16 | 32.8 | |
| THF | | | | 300 mL + 30 mL |
| DI water | | | | 5 mL |

THF: tetrahydrofuran;
DI water: deionized water

Procedure:

DPB was dissolved in 300 mL THF. The turbid solution was filtered through folded filter paper. Potassium hydroxide solution was prepared by dissolving in a mixture of 30 mL THF and 5 mL water. The potassium hydroxide solution was added drop-wise to the DPB solution over a period of 0.5 hour. The potassium salt of DPB formed and precipitated from the solution. The mixture was stirred for about 2 hours at room temperature and then cooled to 4° C. and stirred at that temperature for an additional 2 hours. The product was filtered and washed with cold THF. 10.11 grams wet product was obtained. The collected salt was dried in a vacuum oven at 50° C. to constant weight. Yield: 96.9%.

Lithium Salt

Materials:

| Compound | Molecular weight | Weight (grams) | MMoles | Volumes |
|---|---|---|---|---|
| DPB | 280 | 0.972 | 3.31 | |
| LiOH·H$_2$O | 41.96 | 0.142 | 3.31 | |
| THF | | | | 30 mL + 3 mL |
| DI water | | | | 1 mL |

THF: tetrahydrofuran;
DI water: deionized water

DPB was dissolved in 30 mL THF. The turbid solution was filtered through folded filter paper. Lithium hydroxide solution was prepared by dissolving in a mixture of 3 mL THF and 1 mL water. The lithium hydroxide solution was added drop-wise to the DPB solution over a period of 0.5 hour. The lithium salt of DPB formed and precipitated from the solution. The mixture was stirred for about 2 hours at room temperature and then cooled to 4° C. and stirred at that temperature for an additional 2 hours. The product was filtered and washed with cold THF. 0.92 grams wet product was obtained. The collected salt was dried in a vacuum oven at 50° C. to constant weight. Yield: 97.2%.

Example 2

Further Preparation of Sodium DPB

In Example 1, DPB was dissolved in THF followed by addition of equimolar amount of aqueous sodium hydroxide. This example employs a solution of sodium hydroxide in ethanol (i.e., preparing a 10% NaOH in ethanol).

Procedure (Synthesis in THF):

DPB (7.0 grams) was dissolved in 70 mL THF at room temperature. To the solution was added a solution of 1 gram NaOH (pellets) in 10 mL of absolute ethanol. The resulting solution was stirred at room temperature. Turbidity was immediately observed and mass precipitation was detected within a few minutes. The reaction mixture was then stirred for additional two (2) hours at room temperature. The product was then filtered and washed with 15 mL THF. The wet product was dried at 105° C. under vacuum. Quantitative amounts of DPB were obtained. The purity of the product was 99.2% and the amount of water by Karl Fisher method was 1.26%.

Procedure (Synthesis in Ethanol):

DPB (1.2 gram) was suspended in absolute ethanol and 0.17 gram of NaOH pellets were added at room temperature. The mixture was stirred for about 0.5 hour to complete dissolution. After two (2) additional hours of stirring, half of the ethanol was evaporated (40° C. and 100 mbar) to concentrate the DPB and NaOH, and the product precipitated. The mixture was then cooled to 7° C. and the product was filtered. The cake was not washed to avoid dissolution of the product. Quantitative yield and purity of 99.1% was obtained.

Example 3

Preparation of Salt Form of MMMDPB Sodium Salt 22 grams (68 mmol) of MMMDPB were suspended in 330 mL of t-butyl methyl ether and 10 mL of methanol. The suspension was heated to 60° C. and stirred at such temperature for 30 minutes. Then, 13 mL of 30% solution of sodium methoxide were added drop-wise. During the addition the suspension turned to a clear solution and after some time the product started to precipitate. After the addition of the base was completed, the reaction mixture was cooled to room temperature and stirred for further four hours. Very fine crystals of the sodium salt were obtained after filtration.

The product (NaMMMDPB) was dried at 60° C. in a vacuum oven for three hours. 18.4 grams of dry sodium salt were obtained of which purity by HPLC was determined to be 98.6%. Yield: 78.4%.

Example 4

Sodium Salt of MMMDPB Fails to Increase Bioavailability of MMMDPB and DPB

This study compared the pharmacokinetics of MMMDPB and DPB after oral administrations of MMMDPB (30 mg/kg) and sodium salt of MMMDPB (30 mg/kg) in dogs. Oral suspensions of MMMDPB and sodium salt of MMMDPB were prepared by suspending either MMMDPB or sodium salt of MMMDPB in 2% (w/v) aqueous carobxymethyl cellulose (CMC). Eight (8) Beagle dogs were administered the oral suspensions of MMMDPB or sodium salt of MMMDPB by a single oral gavage.

Blood samples were obtained pre-dose and 0.25, 0.5, 1, 2, 3, 4, 6, 9, 12, 15, 18, and 24 hours after dosing. Venous blood (~1 mL) were drawn and collected in lithium heparin (anti-coagulant). Blood samples were spun in a refrigerated centrifuge and plasma were stored at −80° C. prior to analysis. MMMDPB and DPB were quantified in plasma using HPLC with Tandem Mass Spectrometry detection (LLOQ=0.25 µg/mL). Calibration curves were obtained using a weighted ($1/C^2$) least squares linear regression analysis of peak area ratio (analyte/internal standard) versus the nominal concentration of the calibration standards. Concentrations were obtained by interpolation from the run defined calibration curve. Regressions and figures were generated by PE Sciex Analyst Version 1.2 software.

Plasma samples were thawed and subjected to solid phase extraction with 2 mL acetonitrile prior to HPLC method with Tandem Mass Spectrometry Detection. Chromatographic conditions were performed as followed:

| | |
|---|---|
| Chromatographic mode: | Reversed phase |
| Isocratic/gradient mode: | Isocratic |
| Mobile phase flow rate: | 1 mL/min |
| Back-pressure: | 140 bars (approximately) |
| Autosampler rising vol.: | 1,000 µl |
| Column: | Zorbax SBC18 |
| Retention time: | 2.15 minutes (DPB) |
| | 3.46 minutes (MMMDPB) |

Figure 2:
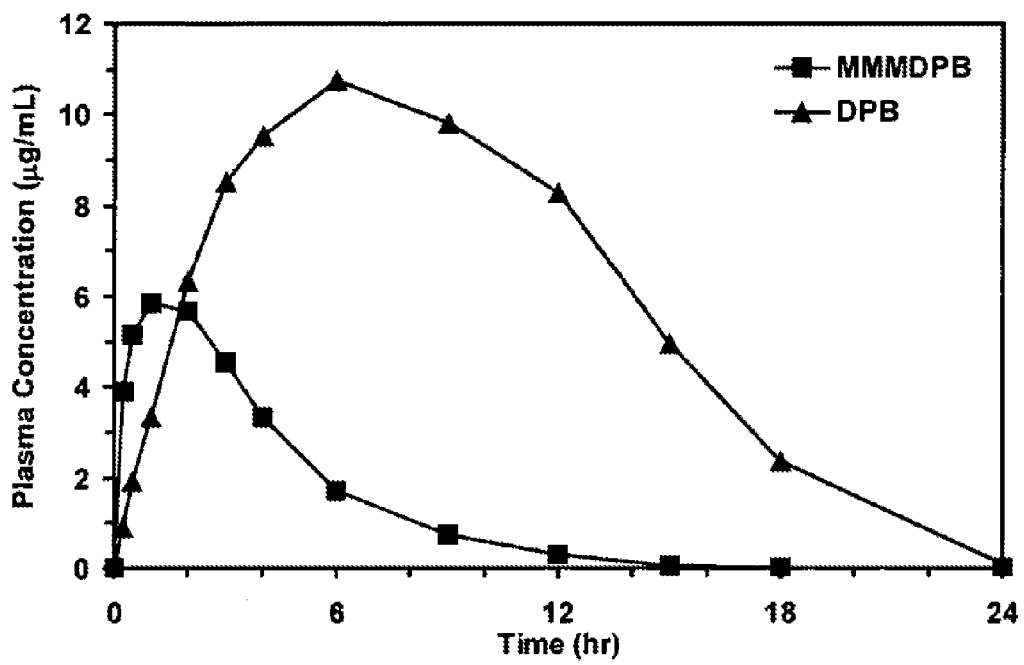
FIG. 2 illustrates the mean plasma concentrations of MMMDPB and DPB after single oral doses of NaMMMDPB in Beagle dogs (30 mg/kg, n=8)
Figure 3:
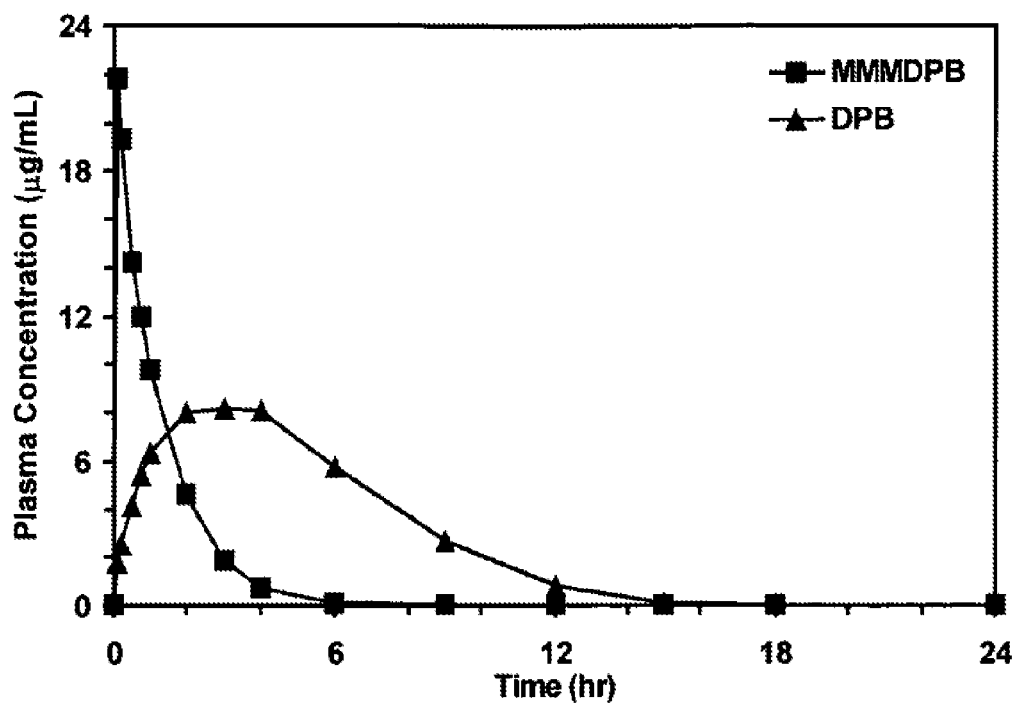
FIG. 3 illustrates the mean plasma concentrations of MMMDPB and DPB after single intravenous infusions of NaMMMDPB in Beagle dogs (15 mg/kg, T=15 min, n=8)

The mean plasma concentrations of MMMDPB and DPB after single oral dosages of MMMDPB (FIG. 1) in Beagle dogs (30 mg/kg) is slightly higher to those of sodium salt of MMMDPB (FIG. 2). The mean plasma concentrations of MMMDPB and DPB after single intravenous infusions of NaMMMDPB in Beagle dogs (15 mg/kg) are shown in FIG. 3.

Table 1 summarizes the mean pharmacokinetic parameters of MMMDPB and DPB after oral administration of MMMDPB and NaMMMDPB and intravenous administration of NaMMMDPB in Beagle dogs (30 mg/kg PO, 15 mg/kg IV, n=8).

The $AUC_{0-t}$ and $C_{max}$ for MMMDPB were lesser after oral administration of sodium salt of MMMDPB, than after oral administration of MMMDPB (29.44 µg·hr/mL vs. 57.41 µg·hr/mL and 6.45 µg/mL vs. 10.22 µg/mL) (See, Table 1).

The $AUC_{0-t}$ and $C_{max}$ for DPB were similarly lesser after oral administration of sodium salt of MMMDPB, than after oral administration of MMMDPB (135.10 µg·hr/mL vs. 193.18 µg·hr/mL and 7.28 µg/mL vs. 9.39 µg/mL) (See, Table 1).

The mean oral bioavailability of MMMDPB was 107% (range 43%-177%) after giving MMMDPB compared with 60% (range 34%-99%) for NaMMMDPB. In other words, the absolute bioavailability (i.e., F value) of MMMDPB after oral administration of MMMDPB is 1.07. The F value of the MMMDPB after oral administration of the sodium salt of MMMDPB is 0.60. The data indicate that the salt form of MMMDPB (i.e., sodium) does not increase the bioavailability of MMMDPB and DPB.

TABLE 1

Mean Pharmacokinetic Parameters of MMMDPB AND DPB after Oral Administration of NaMMMDPB in Beagle Dogs (30 mg/kg, PO, 15 mg/kg IV, n = 8)

| Drug | Route | Dose | Analyte | $C_{max}$ (µg/mL) | $T_{max}$ (hr) | $AUC_{0-t}$ (µg · hr/mL) | $t_{1/2}$ (hr) | F |
|---|---|---|---|---|---|---|---|---|
| MMMDPB | Oral | 30 mg/kg | MMMDPB | 10.22 | 3.25 | 57.41 | 2.59 | 1.07 |
| MMMDPB | Oral | 30 mg/kg | DPB | 13.91 | 9.39 | 193.18 | 4.59 | |
| NaMMMDPB | Oral | 30 mg/kg | MMMDPB | 6.45 | 1.04 | 29.44 | 2.71 | 0.60 |
| NaMMMDPB | Oral | 30 mg/kg | DPB | 11.57 | 7.28 | 135.10 | 3.15 | 3.15 |
| NaMMMDPB | IV Infusion | 15 mg/kg | MMMDPB | 21.91 | 0.113 | 26.17 | 0.78 | — |

TABLE 1-continued

Mean Pharmacokinetic Parameters of MMMDPB AND DPB after Oral
Administration of NaMMMDPB in Beagle Dogs (30 mg/kg, PO, 15 mg/kg IV, n = 8)

| Drug | Route | Dose | Analyte | $C_{max}$ (μg/mL) | $T_{max}$ (hr) | $AUC_{0-t}$ (μg · hr/mL) | $t_{1/2}$ (hr) | F |
|---|---|---|---|---|---|---|---|---|
| NaMMMDPB | IV Infusion | 15 mg/kg | DPB | 8.60 | 3.13 | 59.43 | 2.26 | — |

F is the absolute bioavailability

Thus, these data show that oral administration of sodium salt of MMMDPB fails to increase the bioavailability of DPB.

Example 5

Sodium Salt of DPB Increases Bioavailability of DPB

We examined the delivery of DPB to the vascular compartment by administrating directly DPB and compared it with the sodium salt of DPB in dogs. This study compared the pharmacokinetics of DPB after oral administration of a single dose of DPB (75 mg/kg) or sodium salt of DPB (75 mg/kg) in Beagle dogs. Twenty-eight Beagle dogs were administered DPB and sodium salt of DPB by a single oral gavage (n=24). Blood samples were obtained pre-dose and 0.5, 1, 2, 3, 4, 6, 12, 18, 24, 36 and 48 hours after dosing. DPB was quantified in plasma using HPLC (LLOQ=0.25 μg/mL).

Figure 4:
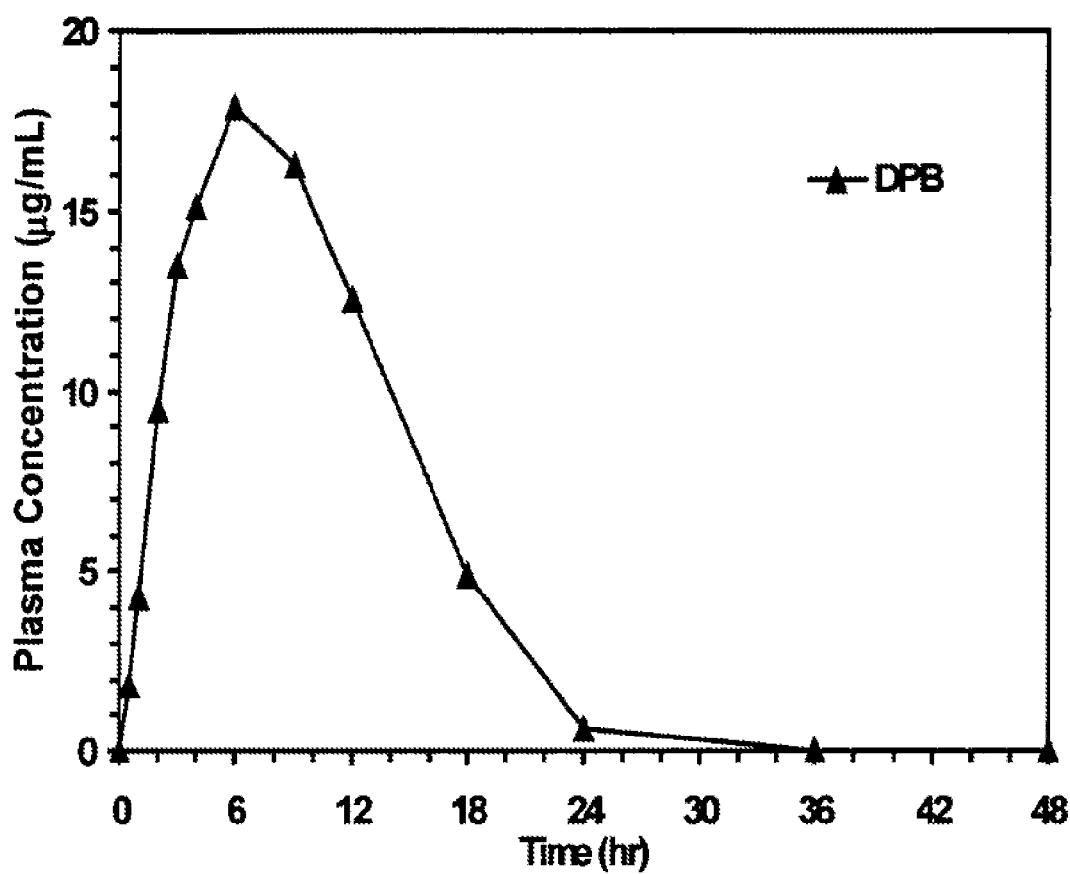
FIG. 4 illustrates the mean plasma concentrations of DPB after single oral doses of DPB in Beagle dogs (75 mg/kg, n=8)
Figure 6:
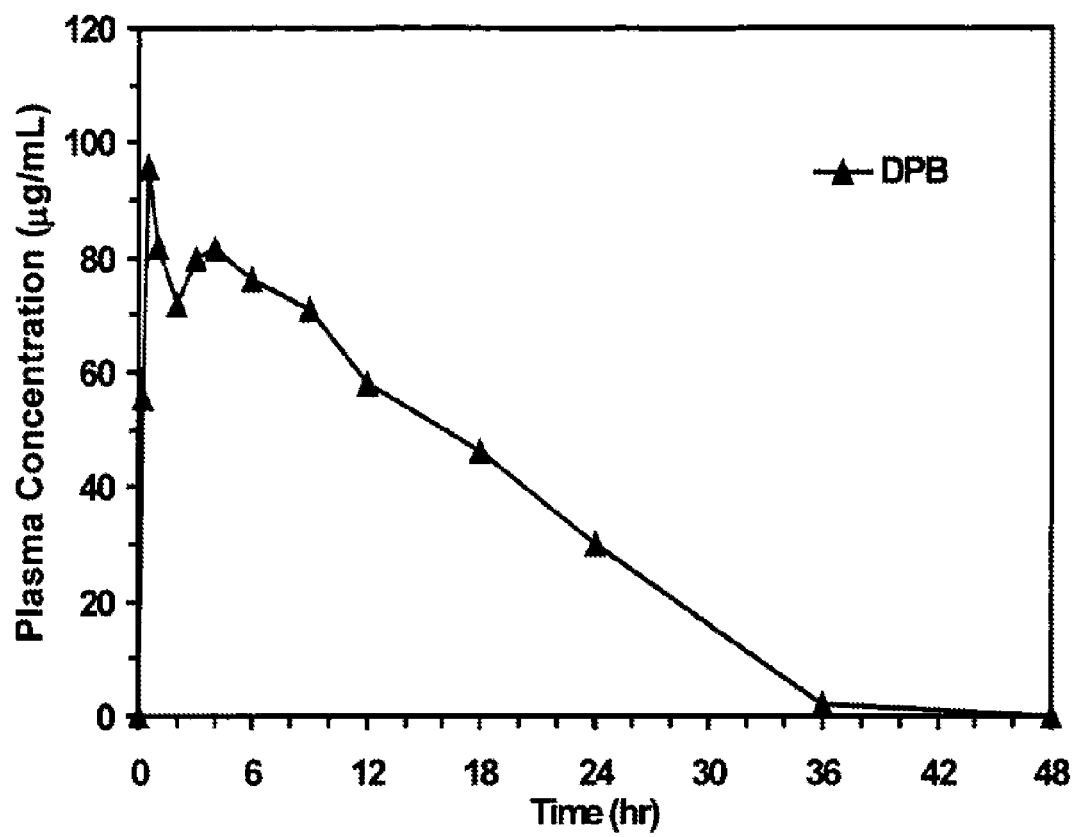
FIG. 6 illustrates the mean plasma concentrations of DPB after single intravenous infusions of NaDPB in Beagle dogs (75 mg/kg, T=30 min, n=4)

The mean plasma concentrations of DPB after single oral dosages of DPB (FIG. 4) in Beagle dogs (75 mg/kg, n=8) is significantly lower to those of sodium salt of DPB (75 mg/kg, n=8) (FIG. 5). The mean plasma concentrations of DPB and DPB after single intravenous (IV) infusions of NaDPB in Beagle dogs (75 mg/kg, T=30 min, n=4)) is shown in FIG. 6.

Table 2 summarizes the mean pharmacokinetic parameters of DPB after oral administration of DPB, NaDPB and intravenous administration of NaDPB in Beagle dogs (75 mg/kg, n=28).

The $AUC_{0-t}$ for DPB was greater (~4 fold) after oral administration of sodium salt of DPB, than after oral administration of DPB (882.8 μg·hr/mL vs. 222.1 μg·hr/mL) (See, Table 2).

The $C_{max}$ for DPB was greater (~3 fold) after oral administration of sodium salt of DPB, than after oral administration of DPB (54.2 μg/mL vs. 18.7 μg/mL) (See, Table 2).

TABLE 2

Mean Pharmacokinetic Parameters of DPB after Oral Administration
of DPB and NaDPB in Beagle Dogs (75 mg/kg, n = 28)

| Drug | Route | Dose | Analyte | $C_{max}$ (μg/mL) | $t_{max}$ (hr) | $AUC_{0-t}$ (μg · hr/ mL) | $t_{1/2}$ (hr) |
|---|---|---|---|---|---|---|---|
| DPB | Oral | 75 mg/kg | DPB | 18.7 | 6.5 | 222.1 | 4.0 |
| NaDPB | Oral | 75 mg/kg | DPB | 54.2 | 7.8 | 882.8 | 5.9 |
| NaDPB | IV Infusion | 75 mg/kg | DPB | 95.7 | 0.5 | 1,574.0 | 6.0 |

These data indicate that administration of the sodium salt of DPB increases the bioavailability of DPB. The mean $AUC_{0-t}$ and $C_{max}$ for DPB were greater after oral and intravenous administration of NaDPB, than after oral administration of DPB. The absolute bioavailability of DPB after administration of NaDPB was about 58%.

Note that in the present study, equal weights of sodium salt of DPB and DPB (i.e., 75 mg/kg) were administered. When the molecular weight of sodium is taken into consideration, there is 6% (more in moles) for DPB as compared to that of sodium salt of DPB. Despite this difference, we surprisingly observed a significant increase in $AUC_{0-t}$ and $C_{max}$ for the sodium salt of DPB.

Example 6

Sodium Salt of DPB Increases Bioavailability of DPB

We calculated $AUC_{0-t}$ for DPB at various times (24, 36 and 48 hours) after oral administrations of DPB and sodium salt of DPB. The data are summarized in the following Table 3.

TABLE 3

AUCs at various times (24, 36 and 48 hours) after Oral Administration of
DPB and NaDPB in Beagle Dogs (75 mg/kg, n = 28)

| Drug | Route | Dose | Analyte | $AUC_{0-24}$ (μg · hr/mL) | $AUC_{0-36}$ (μg · hr/mL) | $AUC_{0-48}$ (μg · hr/mL) |
|---|---|---|---|---|---|---|
| DPB | Oral | 75 mg/kg | DPB | 230.7 | 234.4 | 234.4 |
| NaDPB | Oral | 75 mg/kg | DPB | 882.8 | 962.5 | 962.5 |
| NaDPB | IV Infusion | 75 mg/kg | DPB | 1,411.5 | 1,603.5 | 1,615.4 |

These data indicate that oral administration of the sodium salt of DPB increases the mean $AUC_{0-24}$, $AUC_{0-36}$ and $AUC_{0-48}$ as compared to that after oral administration of DPB.

Example 7

Administration of DPB and Sodium Salt Form of DPB

We examined the delivery of DPB to the vascular compartment by administrating directly DPB and compared it with the sodium salt of DPB. This study compared the pharmacokinetics of DPB after oral administration of DPB (150 mg/kg) and sodium salt of DPB (150 mg/kg) in rats. Fifty-four rats were administered DPB and sodium salt of DPB by a single oral gavage (n=54). Blood samples were obtained (approximately 0.5 mL each) were collected following each treatment from animal via the jugular vein. Blood samplings from groups of 3 rats/sex/time point were collected at various times after dosing, in order to provide the complete time-points of pre-dose, 0, 0.5, 1, 2, 3, 4, 6, 12, 18, 24, 36 and 48 hours after dosing. Each blood sample was collected into a tube containing lithium heparin and the samples were spun in a refrigerated centrifuge. The resultant plasma was stored at −80° C. prior to analysis. DPB was quantified in plasma using HPLC (LLOQ=0.25 μg/mL).

Figure 7:
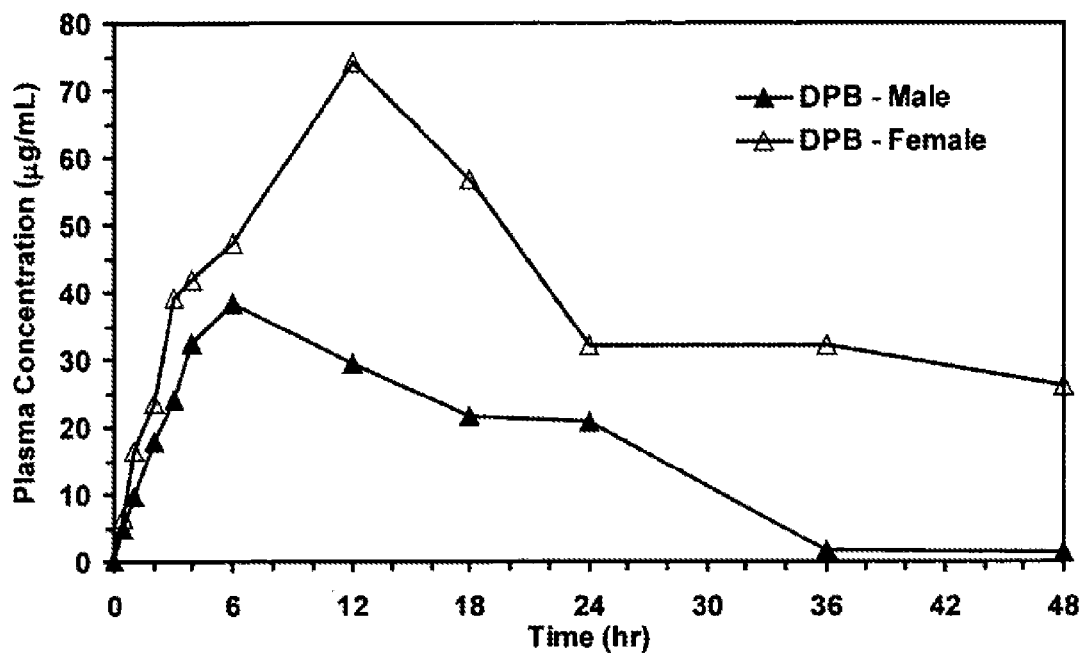
FIG. 7 illustrates the mean plasma concentrations of DPB after single oral doses of DPB in Sprague-Dawley rats (150 mg/kg, n=18)
Figure 8:
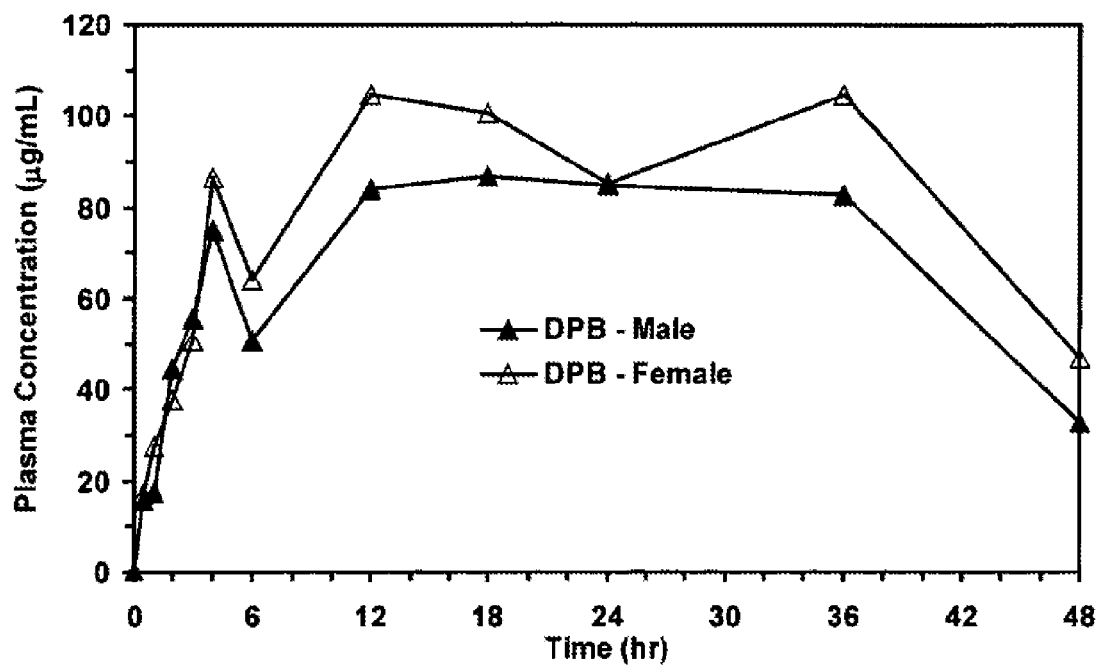
FIG. 8 illustrates the mean plasma concentrations of DPB after single oral doses of NaDPB in Sprague-Dawley rats (150 mg/kg, n=18)
Figure 9:
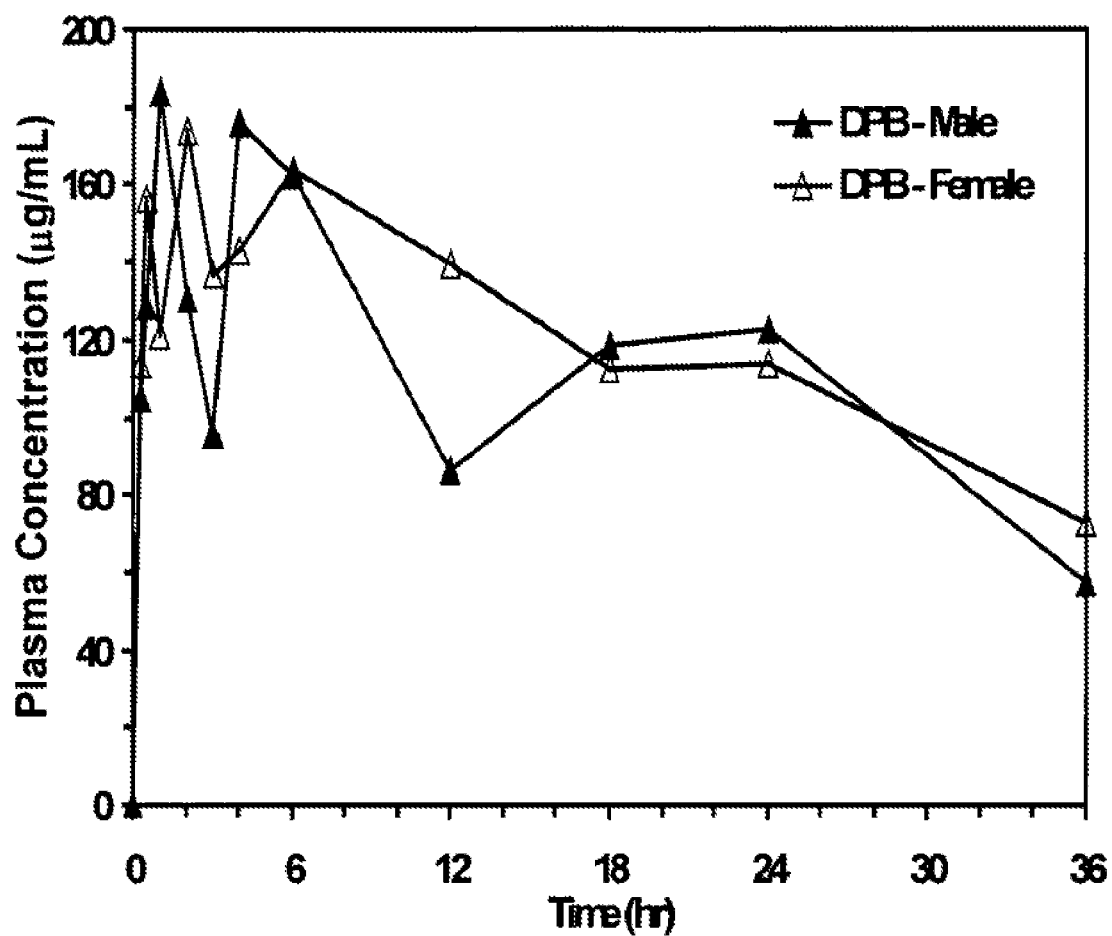
FIG. 9 illustrates the mean plasma concentrations of DPB after single intravenous infusions of NaDPB in Sprague-Dawley rats (150 mg/kg, T=30 min, n=18)

The mean plasma concentrations of DPB after single oral dosages of DPB (FIG. 7) in Sprague-Dawley rats (150 mg/kg, n=18) is significantly lower that that of sodium salt of DPB (150 mg/kg, n=18) (FIG. 8). The mean plasma concentrations of DPB after single intravenous infusions of NaDPB in Sprague-Dawley rats (150 mg/kg, T=30 min, n=18)) is shown in FIG. 9.

Table 4 summarizes the mean pharmacokinetic parameters of DPB after oral administration of DPB and NaDPB, and intravenous administration of NaDPB in Sprague-Dawley rats (150 mg/kg, n=72). For DPB, $AUC_{0-t}$ and $C_{max}$ were greater after oral and intravenous administration of NaDPB compared to DPB.

$AUC_{0-t}$ and $C_{max}$ were greater in females compared to males. As shown in Table 4, the $AUC_{0-t}$ for DPB was greater in male (~4.5 fold) and female (~2 fold) after oral administration of sodium salt of DPB, than after oral administration of DPB (3,414.7 μg·hr/mL vs. 775.5 μg·hr/mL and 4,037.6 μg·hr/mL vs. 1,945.9 μg·hr/mL) (See, Table 4).

The $C_{max}$ for DPB was greater in male (~2.5 fold) and female (~1.5 fold) after oral administration of sodium salt of DPB, than after oral administration of DPB (86.9 μg/mL vs. 38.3 μg/mL and 104.5 μg/mL vs. 74.0 μg/mL) (See, Table 4).

$AUC_{0-t}$ and $C_{max}$ were slightly greater after intravenous administration compared to oral.

The absolute bioavailability (F) of NaDPB in males after oral administration of NaDPB is 70.6. The F value of the NaDPB in females after oral administration of the sodium salt of DPB is 87.7. These data indicate that the salt form of DPB (i.e., NaDPB) greatly increases the absolute bioavailability of DPB.

TABLE 4

Mean Pharmacokinetic Parameters of DPB after Oral Administration of DPB and sodium salt of DPB in Sprague-Dawley Rats (150 mg/kg, n = 72)

| Drug | Route | Dose (mg/kg) | Analyte | Sex | $C_{max}$ (μg/mL) | $t_{max}$ (hr) | $AUC_{0-t}$ (μg · hr/mL) | $t_{1/2}$ (hr) | F |
|---|---|---|---|---|---|---|---|---|---|
| DPB | Oral | 150 | DPB | Male | 38.3 | 6 | 775.5 | 6.6 | — |
|  |  |  |  | Female | 74.0 | 12 | 1,945.9 | 33.2 | — |
| NaDPB | Oral | 150 | DPB | Male | 86.9 | 18 | 3,414.7 | 17.6 | 70.6 |
|  |  |  |  | Female | 104.5 | 12 | 4,037.6 | 32.9 | 87.7 |
| NaDPB | IV Infusion | 150 | DPB | Male | 184.1 | 1 | 4,028.3 | 24.2 | — |
| NaDPB | IV Infusion |  | DPB | Female | 173.8 | 2 | 4,328.0 | 26.8 | — |

F represents the absolute bioavailability

Altogether, these data indicate that administration of sodium salt of DPB greatly increases the bioavailability of DPB.

Example 8

Sodium Salt of DPB Increases Bioavailability of DPB

We calculated $AUC_{0-t}$ for DPB at various times (24, 36 and 48 hours) after oral administrations of DPB and sodium salt of DPB. The data are summarized in the following Table 5.

TABLE 5

AUCs at various times (24, 36 and 48 hours) after Oral Administration of DPB and NaDPB in Beagle Dogs (75 mg/kg, n = 28)

| Drug | Route | Dose (mg/kg) | Analyte | Sex | $AUC_{0-24}$ (μg · hr/mL) | $AUC_{0-36}$ (μg · hr/mL) | $AUC_{0-48}$ (μg · hr/mL) |
|---|---|---|---|---|---|---|---|
| DPB | Oral | 150 | DPB | Male | 623.1 | 757.1 | 775.5 |
|  |  |  |  | Female | 1,211.4 | 1,596.4 | 1,945.9 |

TABLE 5-continued

AUCs at various times (24, 36 and 48 hours) after Oral Administration of
DPB and NaDPB in Beagle Dogs (75 mg/kg, n = 28)

| Drug | Route | Dose (mg/kg) | Analyte | Sex | $AUC_{0-24}$ (μg · hr/mL) | $AUC_{0-36}$ (μg · hr/mL) | $AUC_{0-48}$ (μg · hr/mL) |
|---|---|---|---|---|---|---|---|
| NaDPB | Oral | 150 | DPB | Male | 1,714.7 | 2,720.2 | 3,414.7 |
|  |  |  |  | Female | 1,990.7 | 3,129.5 | 4,037.6 |
| NaDPB | IV Infusion | 150 | DPB | Male | 3,158.1 | 4,607.5 | 5,686.3 |
| NaDPB | IV Infusion |  | DPB | Female | 3,401.8 | 4,757.2 | 5.876.0 |

These data indicate that oral administration of the sodium salt of DPB increases the mean $AUC_{0-24}$, $AUC_{0-36}$, and $AUC_{0-48}$ as compared to that after oral administration of DPB.

Example 9

Sodium Salt of DPB Increases Brain Delivery of DPB

In this study, we measured the brain concentration of DPB. Brains were collected as soon as possible after euthanasia from each rat. They were stored in a freezer at −80° C. prior to determination of DPB brain tissue concentrations. Table 6 summarizes the brain concentrations of DPB after oral administration of DPB and sodium salt of DPB in Sprague-Dawley rats.

Figure 10:
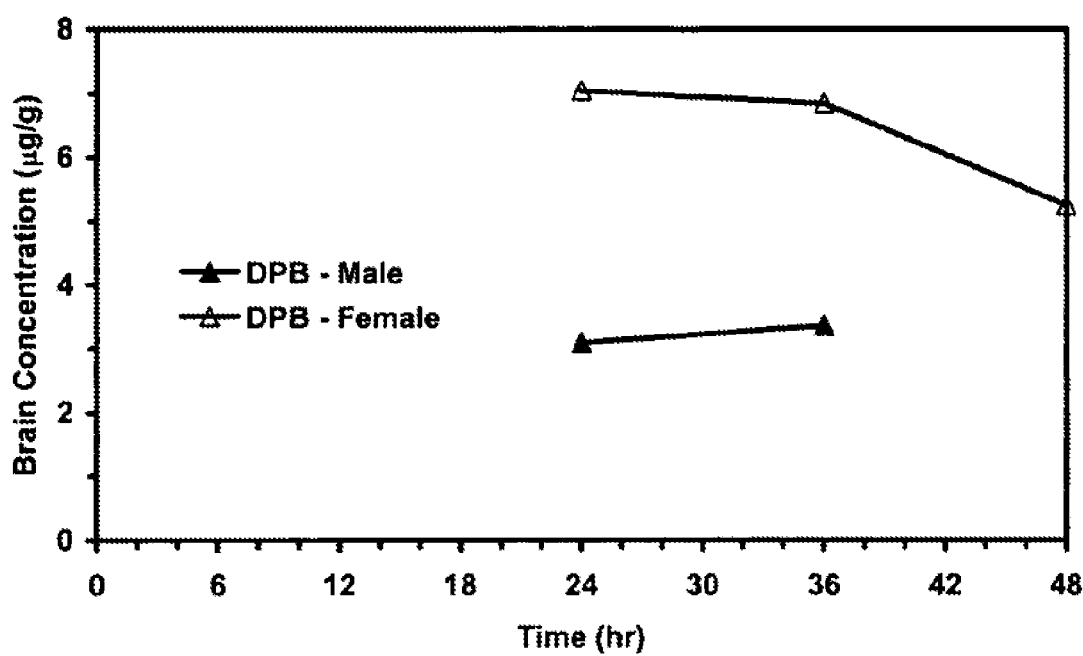
FIG. 10 illustrates the mean brain concentration of DPB after single oral doses of DPB in Sprague-Dawley rats (150 mg/kg, n=18)
Figure 11:
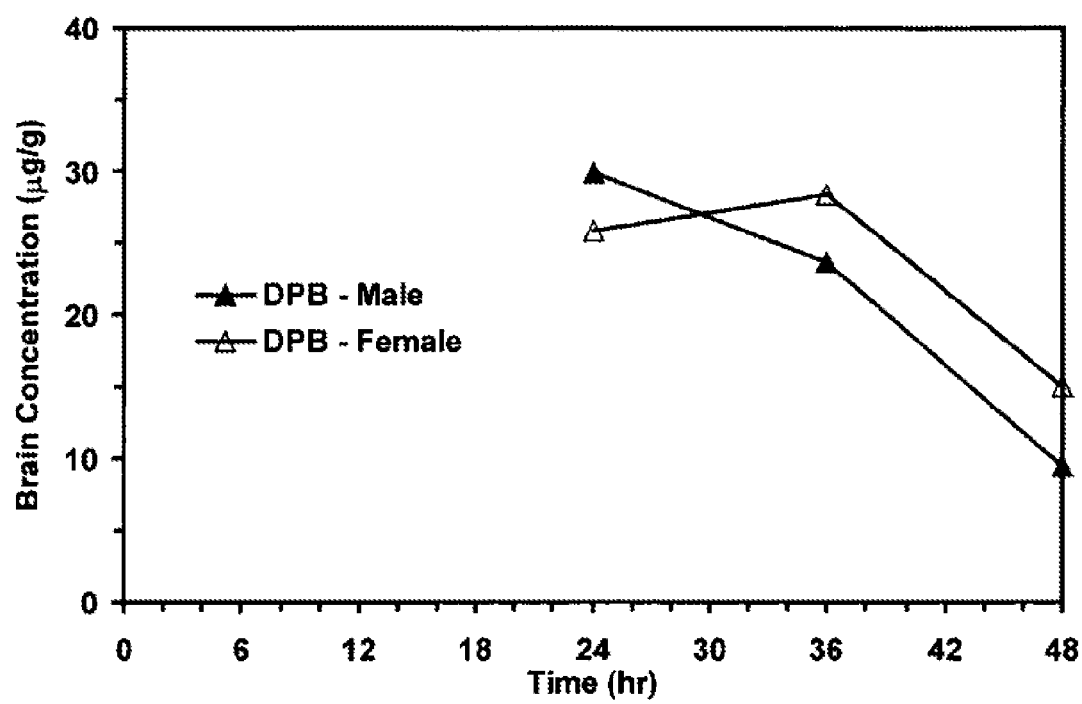
FIG. 11 illustrates the mean brain concentration of DPB after single oral doses of NaDPB in Sprague-Dawley rats (150 mg/kg, n=18)
Figure 12:
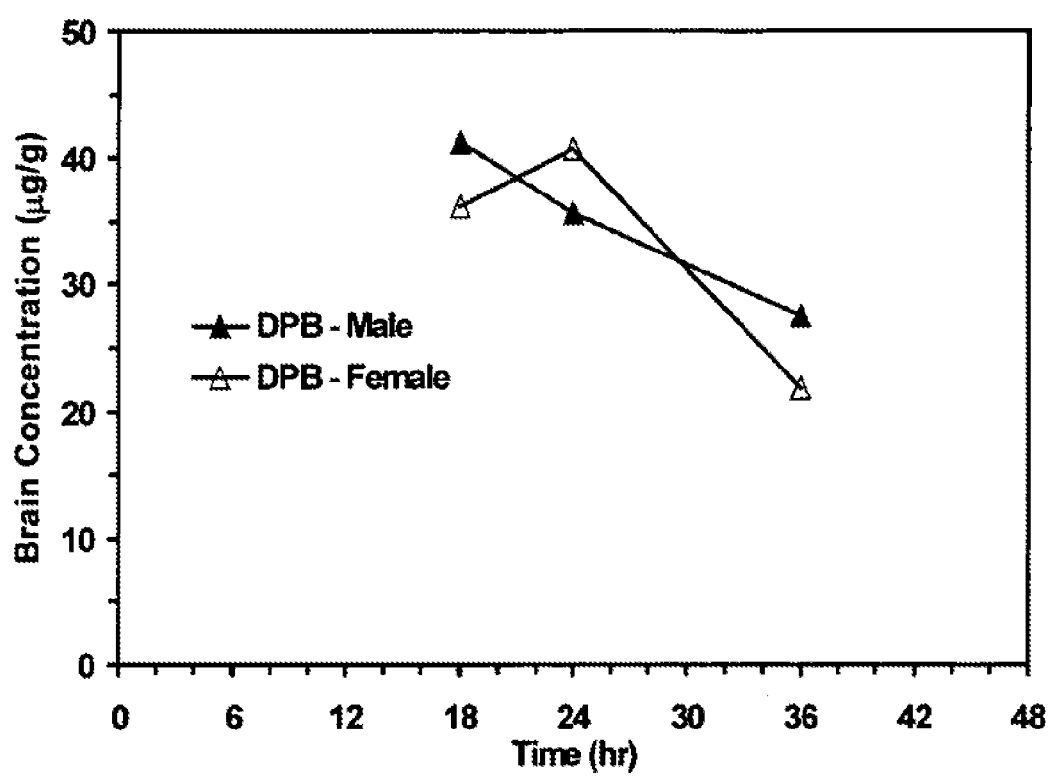
FIG. 12 illustrates the mean brain concentration of DPB after single intravenous infusions of NaDPB in Sprague-Dawley rats (150 mg/kg, T=30 min, n=18)

The mean brain concentrations of DPB after single oral dosages of DPB (FIG. 10) in Sprague-Dawley rats (150 mg/kg, n=18) are significantly lower than those of sodium salt of DPB (150 mg/kg, n=18) (FIG. 11). The mean brain concentrations of DPB after single intravenous infusions of NaDPB in Sprague-Dawley rats (150 mg/kg, t=30 min, n=18) (FIG. 10) are shown in FIG. 12.

As was the case in plasma, brain tissue mean concentrations of DPB are generally greater in female animals than in male animals following administration of NaDPB. As shown in Table 6, the brain concentration of DPB was greater at all the time intervals (i.e., 24, 36 and 48 hours) in male after oral administration of sodium salt of DPB, than after oral administration of DPB (29.91 μg/g vs. 3.09 μg/g; 23.64 μg/g vs. 3.36 μg/g; 9.46 μg/g vs. BQL, respectively) (See, Table 6).

The brain concentration of DPB was also greater at all the time intervals (i.e., 24, 36 and 48 hours) in female after oral administration of sodium salt of DPB, than after oral administration of DPB (25.80 μg/g vs, 7.04 μg/g; 28.40 μg/g vs. 6.84 μg/g; 14.94 μg/g vs, 5.24, respectively) (See, Table 6).

TABLE 6

Mean Brain Concentrations (μg/g) of DPB after Oral
Administration of DPB and Sodium Salt of DPB in
Sprague-Dawley Rats (150 mg/kg, n = 72)

| Drug | Route | Dose | Analyte | Sex | Time (hr) 18 | 24 | 36 | 48 |
|---|---|---|---|---|---|---|---|---|
| DPB | Oral | 150 mg/kg | DPB | Male | — | 3.09 | 3.36 | BQL |
|  |  |  |  | Female | — | 7.04 | 6.84 | 5.24 |
| NaDPB | Oral | 150 mg/kg | DPB | Male | — | 29.91 | 23.64 | 9.46 |
|  |  |  |  | Female | — | 25.80 | 28.40 | 14.94 |
| NaDPB | IV Infusion | 150 mg/kg | DPB | Male | 41.18 | 35.62 | 27.51 | — |
|  |  |  |  | Female | 36.09 | 40.74 | 21.86 | — |

BQL: Below quantification limit,
— not determined

These data indicate that administration of the sodium salt of DPB is rapidly and relatively extensively absorbed from the digestive system, increasing the bioavailability of DPB to the brain at least many fold compared to that seen after oral administration of the free acid form of DPB.

Those skilled in the art will recognize, or be able to ascertain using no more than routine experimentation, many equivalents of the specific embodiments of the invention described herein. The disclosures of the cited publications in the present application are incorporated by reference herein in their entireties by reference. It is to be understood, however, that the scope of the present invention is not to be limited to the specific embodiments described above. The invention may be practiced other than as particularly described and still be within the scope of the accompanying claims.

What is claimed is:

1. A method of improving bioavailability of 5,5-diphenyl barbituric acid in a mammal in need of anti-convulsant treatment, comprising the step of administering to the mammal an oral dosage form that comprises an isolated sodium salt of 5,5-diphenyl barbituric acid, wherein the oral dosage form is solid or a suspension.

2. The method of claim 1, wherein the isolated salt of 5,5-diphenyl barbituric acid is substantially pure.

3. The method of claim 1, wherein the isolated salt of 5,5-diphenyl barbituric acid is at least about 90% pure.

4. The method of claim 1, wherein the method provides an $AUC_{0-48}$ of 5,5-diphenyl barbituric acid of at least 800 μg·hr/mL.

5. The method of claim 1, wherein the method provides an $AUC_{0-48}$ of 5,5-diphenyl barbituric acid of at least 1,200 μg·hr/mL.

6. The method of claim 1, wherein the method provides an $AUC_{0-48}$ of 5,5-diphenyl barbituric acid of at least 1,500 μg·hr/mL.

7. The method of claim 1, wherein the method provides a $C_{max}$ of 5,5-diphenyl barbituric acid of at least 50 µg/mL.

8. The method of claim 1, wherein the method provides a $C_{max}$ of 5,5-diphenyl barbituric acid of at least 75 µg/mL.

9. The method of claim 1, wherein the method provides a $C_{max}$ of 5,5-diphenyl barbituric acid of at least 100 µg/mL.

10. The method of claim 1, wherein the method provides an $AUC_{0-48}$ of 5,5-diphenyl barbituric acid that is at least about 1.5 times greater than that provided by oral administration of the same amount of a free acid form of 5,5-diphenyl barbituric acid.

11. The method of claim 1, wherein the method provides an $AUC_{0-48}$ of 5,5-diphenyl barbituric acid that is at least about 2 times greater than that provided by oral administration of the same amount of a free acid form of 5,5-diphenyl barbituric acid.

12. The method of claim 1, wherein the method provides an $AUC_{0-48}$ of 5,5-diphenyl barbituric acid that is at least about 2.5 times greater than that provided by oral administration of the same amount of a free acid form of 5,5-diphenyl barbituric acid.

13. The method of claim 1, wherein the method provides an $AUC_{0-48}$ of 5,5-diphenyl barbituric acid that is at least about 3 times greater than that provided by oral administration of the same amount of a free acid form of 5,5-diphenyl barbituric acid.

14. The method of claim 1, wherein the method provides an $AUC_{0-48}$ 5,5-diphenyl barbituric acid that is at least about 3.5 times greater than that provided by oral administration of the same amount of a free acid form of 5,5-diphenyl barbituric acid.

15. The method of claim 1, wherein the method provides a $C_{max}$ of 5,5-diphenyl barbituric acid that is at least about 1.5 times greater than that provided by oral administration of the same amount of a free acid form of 5,5-diphenyl barbituric acid.

16. The method of claim 1, wherein the method provides a $C_{max}$ of 5,5-diphenyl barbituric acid that is at least about 2 times greater than that provided by oral administration of the same amount of a free acid form of 5,5-diphenyl barbituric acid.

17. The method of claim 1, wherein the method provides a $C_{max}$ of 5,5-diphenyl barbituric acid that is at least about 2.5 times greater than that provided by oral administration of the same amount of a free acid form of 5,5-diphenyl barbituric acid.

18. The method of claim 1, wherein the salt of 5,5-diphenylbarbituric acid is administered in a sufficient amount to provide a brain concentration of 5,5-diphenylbarbituric acid that is at least about 1.5 times greater than that provided by oral administration of the same amount of a free acid form of 5,5-diphenylbarbituric acid.

19. The method of claim 1, wherein the salt of 5,5-diphenylbarbituric acid is administered in a sufficient amount to provide a brain concentration of 5,5-diphenylbarbituric acid that is at least about 2 times greater than that provided by oral administration of the same amount of a free acid form of 5,5-diphenylbarbituric acid.

20. The method of claim 1, wherein the salt of 5,5-diphenylbarbituric acid is administered in a sufficient amount to provide a brain concentration of 5,5-diphenylbarbituric acid that is at least about 3 times greater than that provided by oral administration of the same amount of a free acid form of 5,5-diphenylbarbituric acid.

21. The method of claim 1, wherein the salt of 5,5-diphenylbarbituric acid is administered in a sufficient amount to provide a brain concentration of 5,5-diphenylbarbituric acid that is at least about 4 times greater than that provided by oral administration of the same amount of a free acid form of 5,5-diphenylbarbituric acid.

22. The method of claim 1, wherein the sodium salt of 5,5-diphenyl barbiturate is administered to provide a brain concentration of 5,5-diphenyl barbituric acid of at least about 20 µg/g at 24 hours after the administration.

23. The method of claim 1, wherein the sodium salt of 5,5-diphenyl barbiturate is administered to provide a brain concentration of 5,5-diphenyl barbituric acid of at least about 20 µg/g at 36 hours after the administration.

24. The method of claim 1, wherein the sodium salt of 5,5-diphenyl barbiturate is administered to provide a brain concentration of 5,5-diphenyl barbituric acid of at least about 8 µg/g at 48 hours after the administration.

25. The method of claim 1, wherein the oral dosage form is a tablet, pill, capsule, caplet, powder, granule, suspension, gel or soft gel.

26. The method of claim 1, wherein the sodium salt of 5,5-diphenyl barbiturate administered is at a dosage from about 0.5 mg/kg to about 100 mg/kg.

27. The method of claim 1, wherein the sodium salt of 5,5-diphenyl barbiturate administered is at a dosage from about 2 mg/kg to about 25 mg/kg.

28. The method of claim 1, wherein the sodium salt of 5,5-diphenyl barbiturate administered is at a dosage from about 3 mg/kg to about 15 mg/kg.

29. The method of claim 1, wherein the sodium salt of 5,5-diphenyl barbiturate administered is at a dosage of about 5 mg/kg to 10 mg/kg.

30. The method of claim 1, wherein the sodium salt of 5,5-diphenyl barbiturate is administered in the amount of from about 30 mg to about 3,000 mg per day.

31. The method of claim 1, wherein the sodium salt of 5,5-diphenyl barbiturate is administered in the amount of from 60 mg to about 1,500 mg per day.

32. The method of claim 1, wherein the sodium salt of 5,5-diphenyl barbiturate is administered in the amount of from 150 mg to about 900 mg per day.

33. The method of claim 1, wherein the sodium salt of 5,5-diphenyl barbiturate is administered in the amount of about 300 mg to about 600 mg per day.

34. The method of claim 1, wherein the mammal is a dog.

35. The method of claim 1, wherein the mammal is a human.

36. A therapeutic method comprising administering an isolated sodium salt of 5,5-diphenyl barbituric acid to a mammal orally in a solid dosage form.

37. The method of claim 36, wherein the sodium salt of 5,5-diphenyl barbiturate administered is at a dosage from about 0.5 mg/kg to about 100 mg/kg.

38. The method of claim 36, wherein the sodium salt of 5,5-diphenyl barbiturate administered is at a dosage from about 2 mg/kg to about 25 mg/kg.

39. The method of claim 36, wherein the sodium salt of 5,5-diphenyl barbiturate administered is at a dosage of about 5 mg/kg to 10 mg/kg.

40. The method of claim 36, wherein the solid dosage form is administered once per day.

41. The method of claim 40, wherein the solid dosage form is administered for at least one week.

42. The method of claim 40, wherein the solid dosage form is administered for at least two weeks.

43. A method of achieving a therapeutic blood level of 5,5-diphenyl barbituric acid in a mammal in need of anticonvulsant treatment, comprising the step of orally administering to the mammal an oral dosage form that comprises isolated sodium salt of 5,5-diphenyl barbituric acid in an amount at least 30% less than the amount of 5,5-diphenyl barbituric acid required to achieve the same therapeutic blood level, wherein the oral dosage form is solid or a suspension.

44. The method of claim 43, wherein the therapeutic blood level is an $AUC_{0-t}$ at least 800 µg·hr/mL.

45. The method of claim 43, wherein the therapeutic blood level is a $C_{max}$ of at least 50 µg/mL.

46. The method of claim 1, wherein the sodium salt of 5,5-diphenyl barbiturate administered is at a dosage of about 50 mg/kg to 150 mg/kg.

47. The method of claim 1, wherein the sodium salt of 5,5-diphenyl barbiturate administered is at a dosage of about 75 mg/kg to 150 mg/kg.

48. The method of claim 36, wherein the sodium salt of 5,5-diphenyl barbiturate administered is at a dosage of about 50 mg/kg to 150 mg/kg.

49. The method of claim 36, wherein the sodium salt of 5,5-diphenyl barbiturate administered is at a dosage of about 75 mg/kg to 150 mg/kg.

* * * * *